United States Patent [19]

Fariss

[11] Patent Number: 5,336,485
[45] Date of Patent: Aug. 9, 1994

[54] METHOD FOR PROTECTING ANIMALS AGAINST TACRINE INDUCED CYTOTOXIC INJURY USING STEROL COMPOUNDS

[75] Inventor: Marc W. Fariss, Manakin-Sabot, Va.

[73] Assignees: Center for Innovative Technology, Herndon; Virginia Commonwealth University, Richmond, both of Va.

[21] Appl. No.: 28,831

[22] Filed: Mar. 10, 1993

Related U.S. Application Data

[63] Continuation of Ser. No. 678,110, Apr. 1, 1991, Pat. No. 5,198,432, which is a continuation-in-part of Ser. No. 316,789, Feb. 28, 1989, abandoned, which is a continuation-in-part of Ser. No. 149,764, Jan. 29, 1988, abandoned.

[51] Int. Cl.$^5$ ............... G01N 33/15; A61K 31/56; A61K 31/44
[52] U.S. Cl. .................. 424/10; 514/182; 514/297
[58] Field of Search ............... 424/10; 514/182, 297

*Primary Examiner*—Gregory Hook
*Attorney, Agent, or Firm*—Whitham, Curtis & Whitham

[57] ABSTRACT

Ionizable congeners of aromatic and aliphatic alcohols provide potent cytoprotective properties in vivo and in vitro. Alpha-tocopherol succinate, cholesteryl succinate, cholesteryl sulfate, dihydrocholesterol succinate, dihydrocholesterol sulfate, and ergosterol analogs are particularly good cytoprotective agents. In addition, the tris salts of these compounds have superior cytoprotective properties.

1 Claim, 23 Drawing Sheets

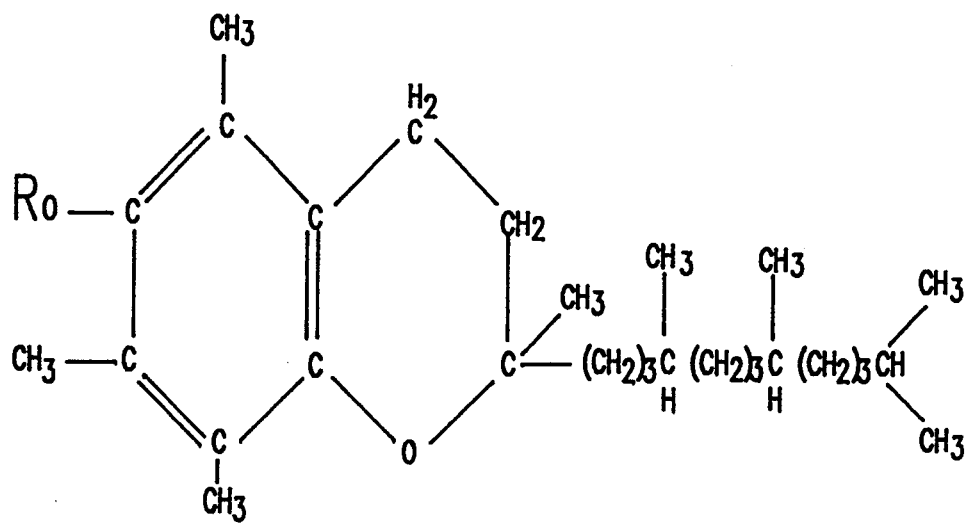

| | ANALOG | CYTOPROTECTION | IONIZABLE ESTER (R GROUP) |
|---|---|---|---|
| R= −P(=O)(OH)−OH | d,α −Tocopheryl phosphate | ++ | Yes |
| R= −C(=O)−(CH)₃−C(=O)−OH | d,α − Tocopheryl glutarate | +++ | Yes |
| R= −C(=O)−(CH)−C(=O)−(O−CH₂−CH₂)ₙ−OH | d,α − Tocopheryl succinate, polyethylene glycol ester | +++ | Yes (only after hydrolysis by esterases) |
| R= −C(=O)−CH−CH(CH₃)−C(=O)−OH | d,α − Tocopheryl 3−methyl succinate | +++ | Yes |
| R= −C(=O)−(CH)₂−C(=O)−OH | d,α − Tocopheryl succinate | ++++ | Yes |

FIG.4A

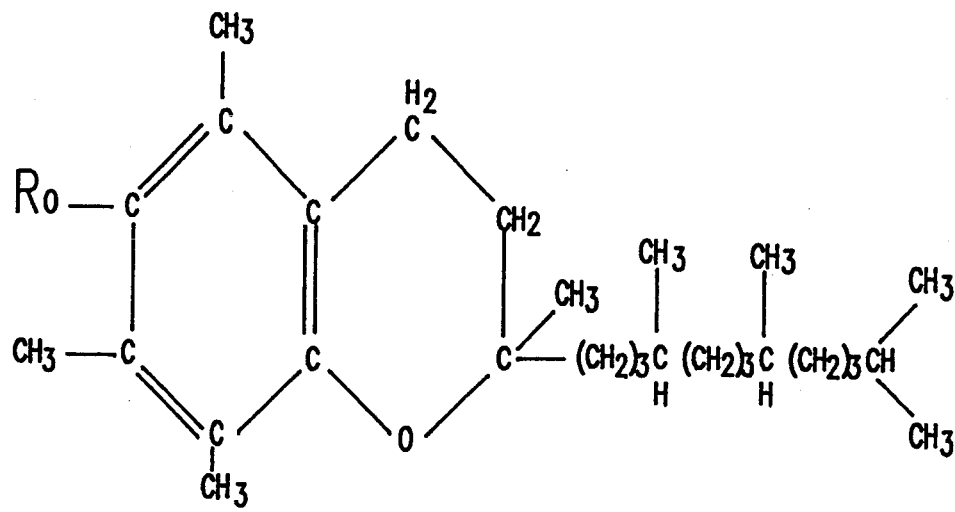

| | ANALOG | CYTOPROTECTION | IONIZABLE ESTER (R GROUP) |
|---|---|---|---|
| R = -C(=O)-CH₃ | d,α- Tocopheryl acetate | - | No |
| R = -H | d,α- Tocopherol | - | untestified |
| R= -C(=O)-(CH)₂-C(=O)-NH₂ (with H) | d,α - Tocopheryl succinamide | +- | Yes (only after deamination by esterases) |
| R= -C(=O)-(CH)₂-C(=O)-O-CH₃ (with H) | d,α - Tocopheryl succinate, methyl ester | ++ | Yes (only after demethylation by esterases) |
| HO-C(=O)-(CH₂)₂-C(=O)-O-[cholesteryl] | Cholesteryl succinate | ++ | Yes |

FIG.4B

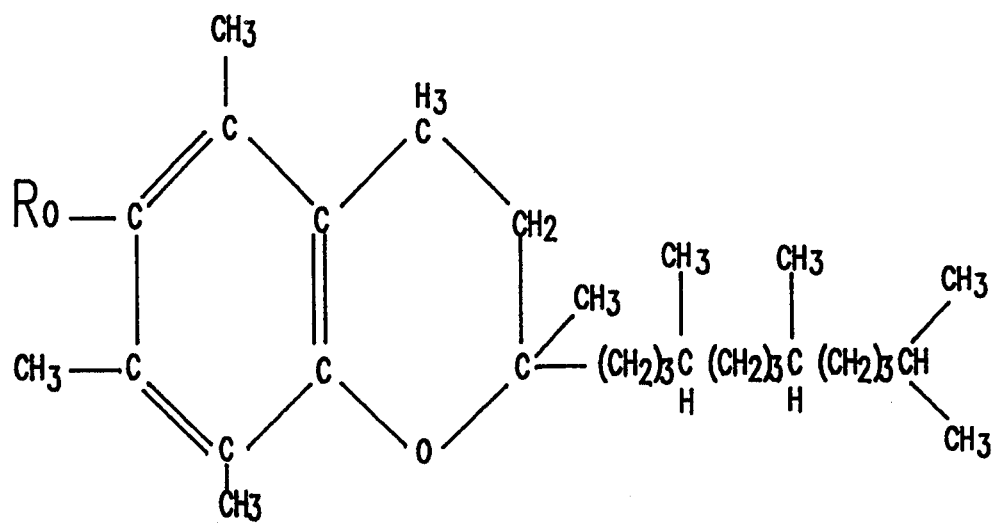

| ANALOG | CYTOPROTECTION | IONIZABLE ESTER (R GROUP) |
|---|---|---|
| d,α- Tocopheryl acetate $R = -\overset{O}{\underset{\|}{C}}-CH_3$ | − | No |
| d,α- Tocopheryl $R = -H$ | − | unesterfied |
| d,α- Tocopheryl phosphate $R = -\overset{O}{\underset{\|}{P}}-OH$ $OH$ | − | Yes |
| d,α- Tocopheryl glutarate $R = -\overset{O}{\underset{\|}{C}}-(C)_3-\overset{O}{\underset{\|}{C}}-OH$ $H$ | − | Yes |
| d,α- Tocopheryl 3-methyl succinate $R = -\overset{O}{\underset{\|}{C}}-\overset{H}{\underset{\|}{C}}-\overset{H}{\underset{\|}{C}}-\overset{O}{\underset{\|}{C}}-OH$ $H\ CH_3$ | − | Yes |

FIG.5A

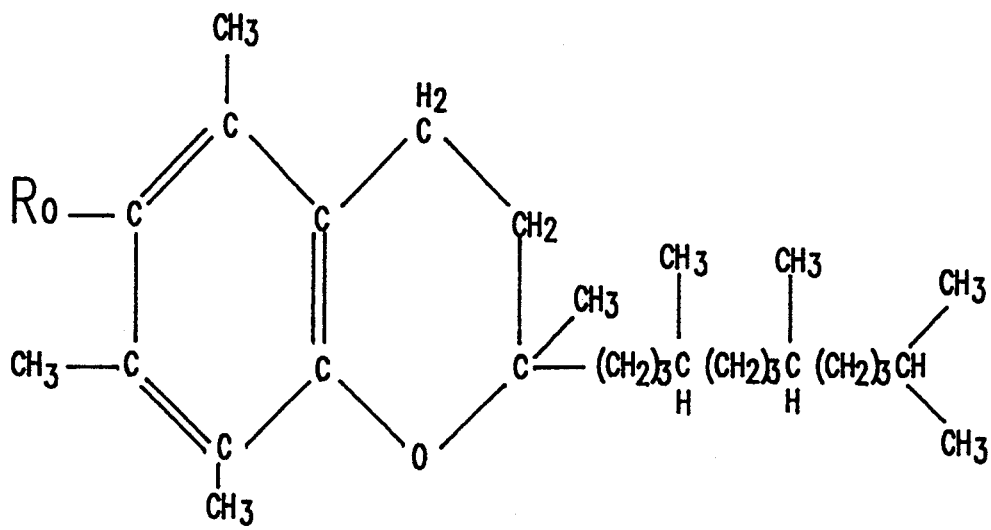
| | ANALOG | CYTOPROTECTION | IONIZABLE ESTER (R GROUP) |
|---|---|---|---|
| 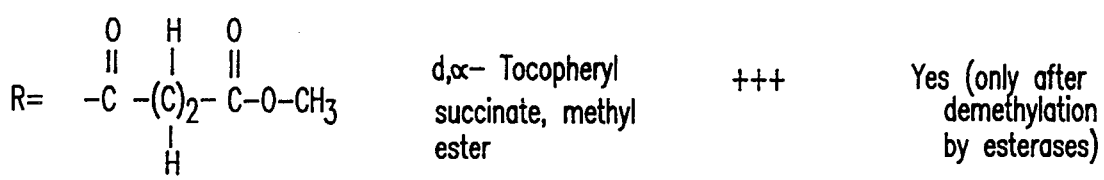 | d,α- Tocopheryl succinate, methyl ester | +++ | Yes (only after demethylation by esterases) |
| 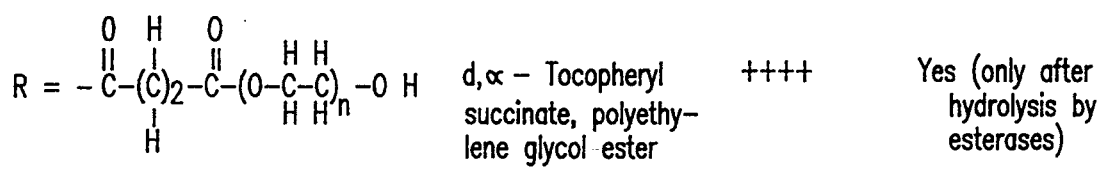 | d,α - Tocopheryl succinate, polyethylene glycol ester | ++++ | Yes (only after hydrolysis by esterases) |
| 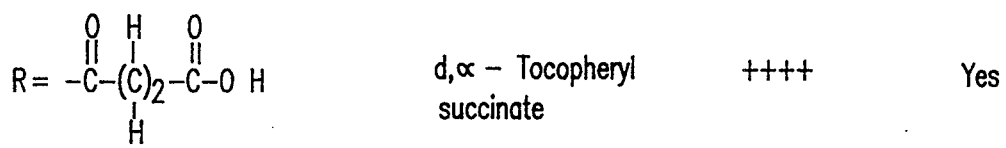 | d,α - Tocopheryl succinate | ++++ | Yes |
| 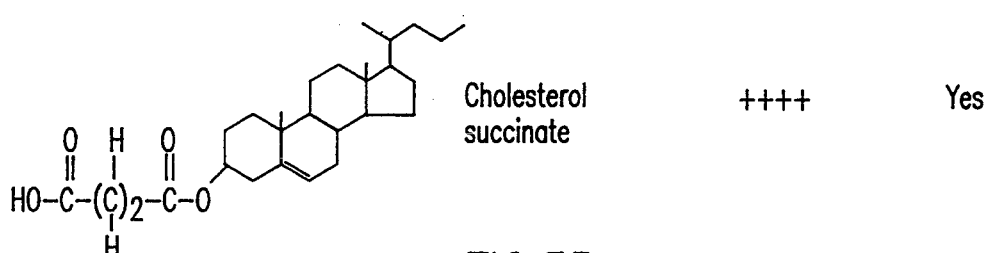 | Cholesterol succinate | ++++ | Yes |
FIG.5B

| R | ANALOG | CYTOPROTECTION | IONIZABLE ESTER (R Group) |
| --- | --- | --- | --- |
| —H | Cholesterol | 0 | No |
| —C(O)—CH$_3$ | Choleteryl acetate | 0 | No |
| —C(O)—(CH$_2$)$_2$—C(O)—O$^-$ tris$^-$ | Cholesteryl succinate tris salt | ++++ | Yes |
| —S(O)$_2$—O$^-$Na$^+$ | Cholesteryl sulfate Sodium salt | +++ | Yes |
| —C(phthalate) $^+$H $^-$O—C(O)— | Cholesteryl hydrogen phthalate | ++++ | Yes |

| R | ANALOG | CYTOPROTECTION | IONIZABLE ESTER (R Group) |
| --- | --- | --- | --- |
| $-H$ | Dihydrocholesterol | 0 | No |
| $-\overset{O}{\underset{\|}{C}}-(CH)_2-\overset{O}{\underset{\|}{C}}-O^-tris^+$ | Dihydrocolesterol succinate, tris salt | ++++ | Yes |
| $-\overset{O}{\underset{\underset{O}{\|}}{\overset{\|}{S}}}-O^-Na^+$ | Dihydrocholesterol Sulfate, sodium salt | ++++ | Yes |

| R | ANALOG | CYTOPROTECTION | IONIZABLE ESTER (R Group) |
| --- | --- | --- | --- |
| −H | Ergosterol | ++ | No |
| $-\overset{O}{\underset{\|}{C}}-(CH)_2-\overset{O}{\underset{\|}{C}}-O^-tris^+$ | Ergosterol succinate, tris salt | +++ | Yes |
| $-\overset{O}{\underset{\underset{O}{\|}}{S}}-O^-K^+$ | Ergosterol Sulfate, potassium salt | +++ | Yes |

| R | ANALOG | CYTOPROTECTION | IONIZABLE ESTER (R Group) |
|---|---|---|---|
| −H | Estrone | ++ | No |
| $-\overset{O}{\underset{\|}{C}}-CH_3$ | Estrone acetate | ++ | No |
| $-\overset{O}{\underset{\|}{C}}-(CH_2)-\overset{O}{\underset{\|}{C}}-O^- H^+$ | Estrone succinate | ++ | Yes |
| $-\overset{O}{\underset{\underset{O}{\|}}{\overset{\|}{S}}}-O^- K^+$ | Estrone sulfate potassium salt | ++ | Yes |

| R | ANALOG | CYTOPROTECTION | IONIZABLE ESTER (R Group) |
| --- | --- | --- | --- |
| $-\overset{O}{\overset{\|}{C}}-(CH_2)_2-\overset{O}{\overset{\|}{C}}-O^-H^+$ | Dehydroepiandosterone 3-succinate | 0 | Yes |
| $-\overset{O}{\underset{O}{\overset{\|}{\underset{\|}{S}}}}-O^-H^+$ | Dehydroepiandosterone 3-sulfate | 0 | Yes |

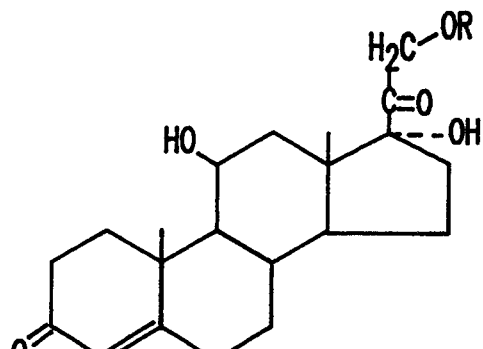
FIG.17A
| R | ANALOG | CYTOPROTECTION | IONIZABLE ESTER (R Group) |
|---|---|---|---|
| $-\overset{O}{\underset{\|}{C}}-(CH_2)-\overset{O}{\underset{\|}{C}}-O^-H^+$ | Hydrocortisone 21-succinate | 0 | Yes |
FIG.17B
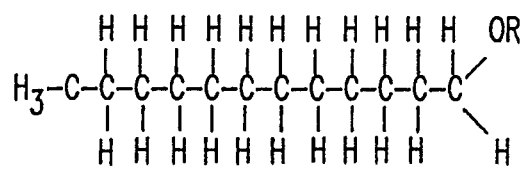
FIG.18A
| R | ANALOG | CYTOPROTECTION | IONIZABLE ESTER (R Group) |
|---|---|---|---|
| $-\overset{O}{\underset{\underset{O}{\|}}{\overset{\|}{S}}}-O^-Na^+$ | Lauryl sulfate Sodium salt | 0 | Yes |
FIG.18B

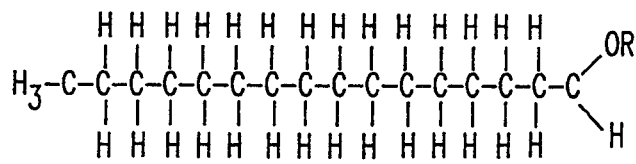
FIG.19A
| R | ANALOG | CYTOPROTECTION | IONIZABLE ESTER (R Group) |
|---|---|---|---|
| –H | Palmityl alcohol | 0 | No |
| $-\overset{O}{\overset{\|}{C}}-(CH_2)-\overset{O}{\overset{\|}{C}}-O^-H^+$ | Palmityl succinate | 0 | Yes |
FIG.19B
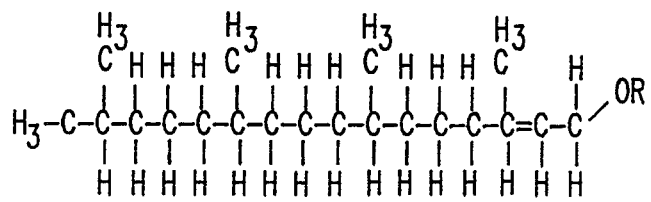
FIG.20A
| R | ANALOG | CYTOPROTECTION | IONIZABLE ESTER (R Group) |
|---|---|---|---|
| –H | Phytol | 0 | No |
| $-\overset{O}{\overset{\|}{C}}-(CH_2)-\overset{O}{\overset{\|}{C}}-O^-H^+$ | Phytol succinate | 0 | Yes |
FIG.20B

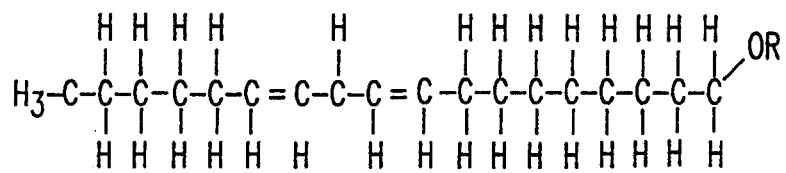
FIG.21A
| R | ANALOG | CYTOPROTECTION | IONIZABLE ESTER (R Group) |
|---|---|---|---|
| – H | Linoleyl alcohol | – (potential toxicity) | No |
| 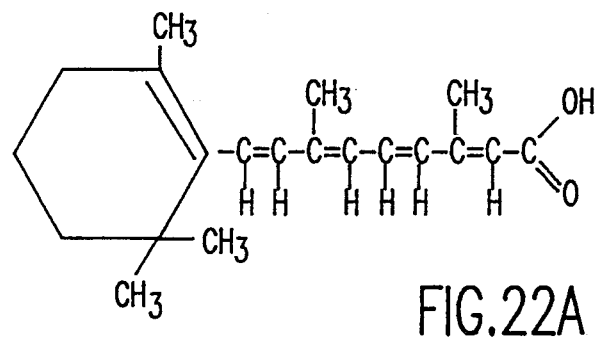 | Linoleyl succinate | + | Yes |
FIG.21B
FIG.22A
RETINOIC ACID
| ANALOG | CYTOPROTECTION | IONIZABLE ESTER (R Group) |
|---|---|---|
| Retinoic acid | – (potential toxicity) | Yes |
FIG.22B

METHOD FOR PROTECTING ANIMALS AGAINST TACRINE INDUCED CYTOTOXIC INJURY USING STEROL COMPOUNDS

CROSS-REFERENCE TO RELATED APPLICATIONS

This application is a continuation of application 678,110 filed Apr. 1, 1991 now U.S. Pat. No. 5,198,432 continuation-in-part of the co-pending patent application having Ser. No. 07/316,789, filed Feb. 28, 1989,now abandoned which is a continuation-in-part of the patent application having Ser. No. 07/149,764, filed Jan. 29, 1988, now abandoned.

DESCRIPTION

BACKGROUND OF THE INVENTION

1. Field of the Invention

The subject invention generally relates to preventing cell injury and death and, more particularly, to administering ionizable congeners of aromatic and aliphatic alcohols to animals for therapeutic and prophylactic purposes including preventing carcinogenesis.

2. Description of the Prior Art

In general terms, cell injury is characterized by changes in cellular metabolic performance and alterations in cellular structure. Cell injury is assumed to be reversible upon termination of the insult or by the addition of a cytoprotective agent during the early stages; however, if the insult continues unchecked, the cell becomes non-functional and unrecoverable. Irreversible cell injury equates to cell death.

The pathological and physiological consequences of cell injury affect the functional and structural integrity of tissue and organ systems as well as the organism itself. Both endogenous and exogenous "insults"can cause cell injury. Endogenous insults are cellular factors, and they include the formation of reactive intermediates (i.e., oxygen free radicals generated during cellular electron transport processes), reduction in oxygen tension (i.e., in ischemia), and stimulation of inflammatory and immune processes. Exogenous insults are environmental factors, and they include exposure to drugs or chemicals, physical stimuli (i.e., radiation), or biological hazards (i.e., viruses).

Recent studies suggest that endogenous and exogenous insults cause cellular injury predominantly by generating reactive intermediates such as free radicals. The majority of reactive intermediates formed during cell or tissue injury are oxygen free radicals such as superoxide anion, hydroxyl free radical, or singlet oxygen and reactive oxygen containing compounds such as hydrogen peroxide. Once formed, both chemical and oxygen derived free radicals can react with a variety of cellular constituents including proteins, nucleic acids, and membrane lipids.

Cells contain endogenous protective systems to ensure viability and promote metabolic performance. For example, alpha-tocopherol is a free radical scavenger present in cellular membranes which binds free radicals in the cell. Alpha-tocopherol, which is often referred to as Vitamin E, is believed to protect against a variety of pathological processes including carcinogenesis, aging, chemical-induced toxicity, radiation-induced toxicity, ischemia-induced damage, and atherosclerosis. Alpha-tocopherol is not synthesized in mammalian cells, but rather, is derived from exogenous sources. Because unesterfied alpha-tocopherol is readily degraded when exposed to oxygen in the air, an ester derivative of alpha-tocopherol (alpha-tocopheryl acetate), is commonly used to provide a stable dosage form of alpha-tocopherol. Cellular esterases release the alpha-tocopherol in the cell by degrading the ester linkage.

The administration of succinate in high concentrations can protect cells from a variety of toxic insults. Providing the cell with additional quantities of succinate, a substrate in the tricarboxylic acid cycle, can result in energy production from oxidative phosphorylation and glycolysis which produce adenosine triphosphate (ATP) and result in glucose production from gluconeogenesis. Kondrashova et al., *Biochem. Biophys. Res. Comm.* 109:376 (1982), reported that the addition of 6 mM succinate to isolated rat liver mitochondria increased the $Ca^{2+}$ capacity and $Ca^{2+}$ retention of mitochondria five to seven fold. Cellular absorption and accumulation of succinate is limited by the polarity of the succinate molecule except in the kidney where a transport system exists. Rognstad, *Arch. Biochem. Biophys.* 230:605, (1984), has shown the cellular uptake of succinate can be advanced by administering a more lipophilic form of succinate (i.e., methyl ester of succinate). Cellular esterases will release the succinate moiety by degrading the ester linkage. Millimolar concentrations of succinate or methyl ester succinate are required to stimulate gluconeogenesis or ATP production to provide cytoprotection (See, Rognstad, *Arch. Biochem. Biophys.* 230:605 (1984) and Sanders, *Proc. Soc. Exp. Biol. Med.* 130:1021, (1969)).

SUMMARY OF THE INVENTION

It is an object of this invention to provide a method for protecting cells from cell injury and death.

It is another object of this invention to provide a method for wound healing and promoting cell recovery.

It is another object of this invention to prevent carcinogenesis.

It is another object of this invention to provide a method for using ionizable congeners of aromatic and aliphatic alcohols to prevent cell injury and death in vitro and in vivo.

It is another object of this invention to provide increased efficacy for aromatic and aliphatic alcohols by providing tris salt derivatives.

It is another object of this invention to use dihydrocholesterol succinate, dihydrocholesterol sulfate, cholesteryl sulfate, ergosterol succinate, and ergosterol sulfate as cytoprotective agents.

It is another object of this invention to provide a method for using ionizable tocopheryl congeners for preventing cell injury and death.

It is another object of this invention to provide a method for using alpha tocopherol succinate to prevent cell injury and death.

It is another object of this invention to provide a method for using cholesteryl succinate to prevent cell injury and death.

It is another object of this invention to provide a method for retarding or preventing aging.

It is another object of this invention to provide a method for preventing lipid peroxidation.

It is yet another object of this invention to convert certain toxic drug compounds to non-toxic, protective drugs by converting alcohol moieties to ionizable congeners.

According to the invention, experiments have been performed in vitro and in vivo which show that ionizable congeners of aromatic and aliphatic alcohols are effective cytoprotective agents. The term "ionizable congener" refers to ionizable ester and ionizable ether derivatives (including alpha, beta, delta and gamma derivatives of tocopherol and their isomers) which have an ionizable side chain or a side chain that is ionizable upon cellular accumulation. Examples of suitable ionizable congeners of aromatic and aliphatic alcohols include tocopheryl succinate (TS) and cholesteryl succinate. Unesterfied tocopherol and tocopheryl acetate (TA) are not ionizable congeners. Cholesteryl succinate has been shown to be anticarcinogenic.

BRIEF DESCRIPTION OF THE DRAWINGS

The foregoing and other objects, aspects and advantages of the invention will be better understood from the following detailed description of the preferred embodiments of the invention with reference to the accompanying drawings, in which:

FIGS. 4a–4b are diagrams showing the chemical formulas of tocopherol congeners and contrasting the structure versus activity relationships observed in vitro;

FIGS. 5a–5b are diagrams showing the chemical formulas of tocopherol congeners and contrasting the structure versus activity relationships observed in vivo;

FIGS. 12a–b to 11a–b are chemical structures and tables showing the cytoprotective properties of various substituents of the chemical structures, respectively.

BRIEF DESCRIPTION OF THE TABLES

Figure 1A:
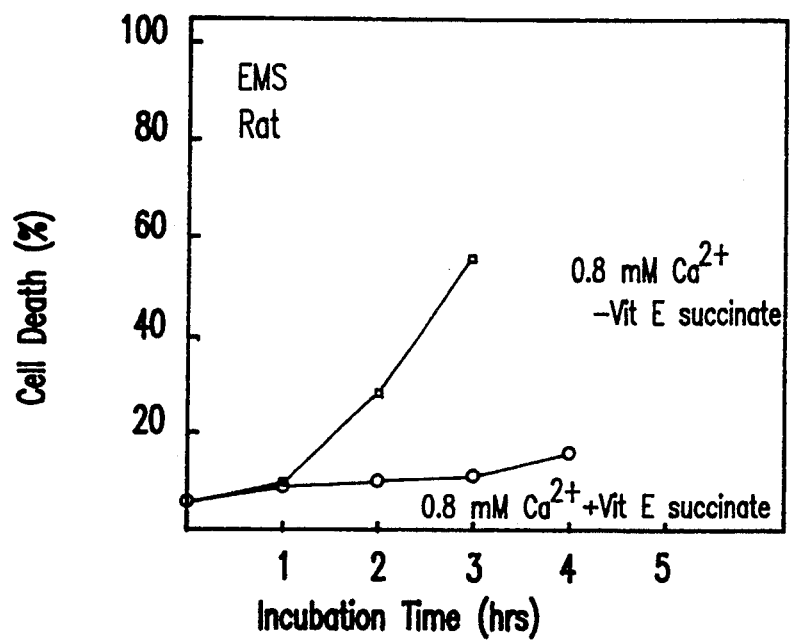
FIGS. 1a–1d are graphs showing the protective effect of alpha-TS on drug-induced liver cell death under physiological conditions.

Table 1 shows free and total calcium content of rat serum and cell culture medium from rate hepatocyte suspensions;

Table 2 shows the protective effect of tocopherol analogs on chemical induced toxicity and lipid peroxidation in rat liver hepatocyte suspensions;

Table 3 shows the protective effect of tocopherol analogs on carbon tetrachloride ($CCl_4$) induced lethality in rats;

Table 4 shows liver specific enzyme levels in rat plasma 48 hours after $CCl_4$ administration;

Table 5 shows the concentrations of alpha-tocopherol and alpha-tocopherol ester in rat liver 24 hours after tocopherol analog administration in vivo;

Table 6 shows tissue distribution of alpha-tocopherol and alpha-tocopherol succinate 24 hours after a 100 mg/kg dose of alpha-tocopherol succinate;

Table 7 shows the protective effect of tocopherol and succinate analogs on $CCl_4$ induced lethality in rates;

Table 8 shows the protective effect of d-alpha-tocopherol succinate on rate hepatocytes exposed to a variety of toxic insults;

Table 9 shows liver specific enzyme levels in rat plasma 24 hours after acetaminophen administration;

Table 10 shows the protective effect of dl-alpha-tocopheryl phosphate on chemical induced toxicity and lipid peroxidation in cultured rate hepatocytes;

Table 11 shows the effect on tocopherol analog dose on the concentration of alpha-T and alpha-TS and on cytoprotection in rate hepatocytes exposed to EMS for 3 hours;

Table 12 shows the protective effect of tocopherol and succinate analogs on EMS-induced toxicity in rat hepatocytes;

Table 13 shows the effect of esterase inhibitors on alpha-TS medicated protection in hepatocyte suspensions exposed to EMS;

Table 14 shows the effect of tocopherol analogs and succinate on the ATP content of hepatocyte during a 6 hour incubation;

Table 15 shows the effect of succinate derivatives on EMS induced toxicity in ray hepatocytes suspensions;

Table 16 shows the effect of alpha-tocopherol succinate (+) or vehicle (−) administration on the energy status of rat tissue;

Table 17 shows the protective effect of tocopherol and succinate analogs on carbon tetrachloride induced lethality in rats;

Table 18 shows the in vivo results of $CCl_4$ induced lethality and hepatoxicity in rats pretreated with various tocopherol and succinate analogs;

Table 19 shows in vivo survival times of CDF1 mice following an injection of 106 L1210 leukemia cells where certain groups of mice were treated with alpha-TS tris salt or cholesteryl succinate tris salt;

Table 20 shows alpha-TS tris salt and cholesteryl succinate tris salt protection in vivo against $CCl_4$ induced hepatotoxicity;

Table 21 shows the in vivo protective effect of cholesteryl succinate against damage from total ischemia;

Table 22 shows the in vivo protective effect of cholesteryl succinate against damage from partial ischemia;

Table 23 shows the in vivo protective effect of cholesteryl succinate against acetaminophen-induced hepatotoxicity;

Table 24 shows the in vivo effects of pretreatment with cholesteryl succinate on tremors, salivation, an survival when animals are subjected to a THA challenge;

Table 25 shows the effects of tocopheryl succinate and cholesteryl succinate pretreatment on the pentobarbitone sleeping time in vivo;

Tables 26 and 27 show in vivo the protective capacity of cholesteryl succinate in the free acid and tris salt forms and alpha tocopherol succinate in the free acid and tris salt forms, respectively, against $CCl_4$-induced hepatotoxicity;

Table 28 shows in vivo the protective capacity of varying concentrations of cholesteryl succinate against CCl4-induced hepatotoxicity;

Table 29 shows in vivo the effect of pretreatment time on cholesteryl succinate tris salt-mediated protection against CCl4 hepatotoxicity;

Table 30 shows in vivo the effects of various ionizable congeners of aromatic and aliphatic alcohols on CCl4 hepatotoxicity;

Table 31 shows in vivo the effects of cholesterol analogs on CCl4 hepatotoxicity;

Table 32 shows in vivo the effects of alpha-TS and cholesteryl succinate tris salt on CCl4 hepatotoxicity when administered using polyethylene glycol as the vehicle;

Table 33 shows in vivo the effects of tris succinate, cholesteryl 3-sulfate, palmityl succinate, palmityl alcohol, and hydrocortisone 21-succinate on CCl4 hepatotoxicity;

Table 34 shows in vivo the effects of cholesteryl succinate tris salt, estrone sulfate potassium salt, dehydroepiandrosterone 3-sulfate sodium salt, cholesterol hydrogen phthalate, and dehydrocholesterol sulfate on CCl4 hepatotoxicity;

Table 35 shows in vivo the effects of dehydrocholesterol sulfate sodium salt, dehydrocholesterol plus sodium sulfate, linoleyl succinate, and linoleyl alcohol on CCl4 hepatotoxicity;

Table 36 shows in vivo the effect of dehydrocholesterol succinate on CCl4 hepatotoxicity;

Table 37 shows in vivo the effects of cholesteryl succinate tris salt, dehydrocholesterol succinate tris salt, phytol succinate, and phytol on CCl4 hepatotoxicity;

Table 38 shows in vivo the effect of ergosterol, ergosterol sulfate potassium salt, and ergosterol succinate tris salt on CCl4 hepatotoxicity;

Table 39 shows in vivo the effect of dehydroepiandrosterone 3-succinate, linoleyl succinate, and ergosterol on CCl4 hepatotoxicity;

Table 40 shows in vivo the effect of estrone 3-succinate and lauryl sulfate sodium salt on CCl4 hepatotoxicity;

Table 41 shows in vivo the effect of retinoic acid and retinol acetate on CCl4 hepatotoxicity;

Table 42 shows in vivo the effect of estrone, estrone acetate and estrone succinate on CCl4 hepatotoxicity.

DETAILED DESCRIPTION OF THE PREFERRED EMBODIMENTS OF THE INVENTION

Experiments have been performed in vitro and in vivo which show that under physiological conditions, ionizable congeners of aromatic and aliphatic alcohols protect mammalian cells from cell injury and death.

Previous studies by the inventor, Fariss, *Science* 227:751, (1985) and Pascoe, *Arch. Biochem. Biophys.* 256:159, (1987) demonstrated that rat hepatocytes could be protected from the toxic effects of drugs by incubating these cells in a $Ca^{2+}$ free medium with d-alpha-tocopheryl succinate (alpha-TS). The addition of 3.5 mM $Ca^{2+}$ to the medium, however, eliminated the cytoprotective effect of alpha-TS. The physiological relevance of results obtained from in vitro studies using abnormally low (0 mM) or abnormally high (3.5mM) extracellular $Ca^{2+}$ concentrations is unclear. The extracellular calcium concentrations (0 and 3.5 mM) were selected to test a hypothesis proposed by Farber, *Life Sci.* 29:1289, (1981) on the importance of extracellular $Ca^{2+}$ in toxic cell injury (See, Fariss, *Toxicol. Appl. Pharmacol.* 79: 296, (1985)), and not for the purpose of simulating or predicting cytoprotection in vivo.

To determine the $Ca^{2+}$ concentration in cell culture medium needed to simulate physiological conditions, the $Ca^{2+}$ content of serum, the in vivo cell perfusate, was examined. Table 1 shows the measured free and total calcium content of rat serum and cell culture medium from rate hepatocyte suspension.

TABLE 1

Free and Total Calcium Content of Rat Serum and Cell Culture Medium from Rat Hepatocyte Suspensions

| Specimen | Calcium Concentration | |
|---|---|---|
| | Total[b] | Free[c] |
| 1. Rat Serum | 5.2 ± 0.1 | 1.2± 0.1 |
| 2. Cell Culture Medium[d] From Hepatocyte Suspensions | | |
| a) No Additions ($Ca^{2+}$ Free) | <0.1 | <0.1 |
| b) +0.8 mM $CaCl_2$ | 0.9 ± 0 | 0.8 ± 0.2 |
| c) +3.5 mM $CaCl_2$ | 3.5 ± 0.1 | 3.0 ± 0.2 | a) Results are expressed as X ± SE of 3 to 5 separate specimens.
b) As measured with atomic absorption spectroscopy.
c) As measured with a calcium electrode.
d) $Ca^{2+}$ free Waymouth 751/2 medium The total $Ca^{2+}$ content of rat serum is approximately 5 mM which comprises approximately 1 mM free $Ca^{2+}$ and 4 mM plasma protein bound $Ca^{2+}$. thus, mammalian cells in vivo are maintained in an environment (serum) in which approximately only 1 mM $Ca^{2+}$ is available for exchange with cells while the remainder is bound and unavailable. Because of calcium's regulatory role in the cell, the concentration of free $Ca^{2+}$ in serum is tightly controlled to prevent fluctuations. In vitro model systems should therefore have a concentration of free $Ca^{2+}$ of approximately 1 mM to simulate physiological conditions. All in vitro studies performed by the inventor were performed under physiological conditions.

Figure 1B:
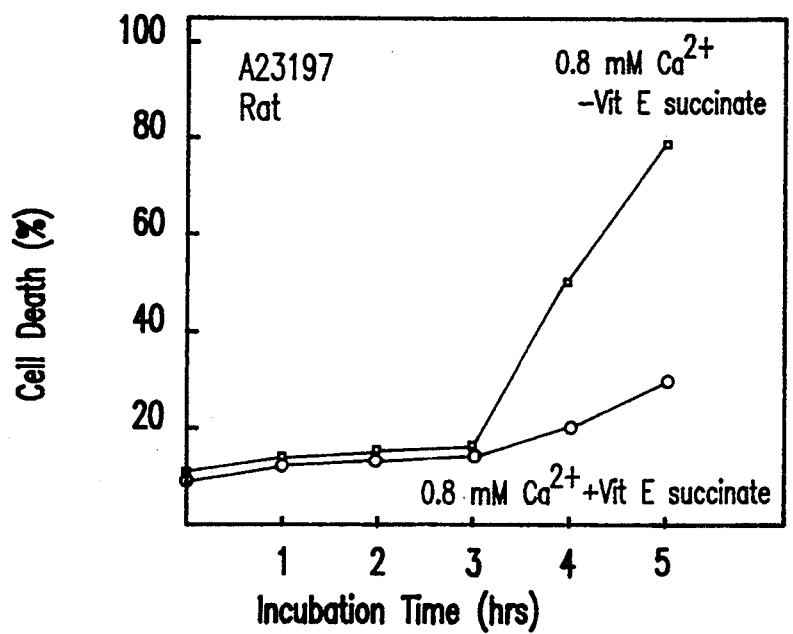
Figure 1C:
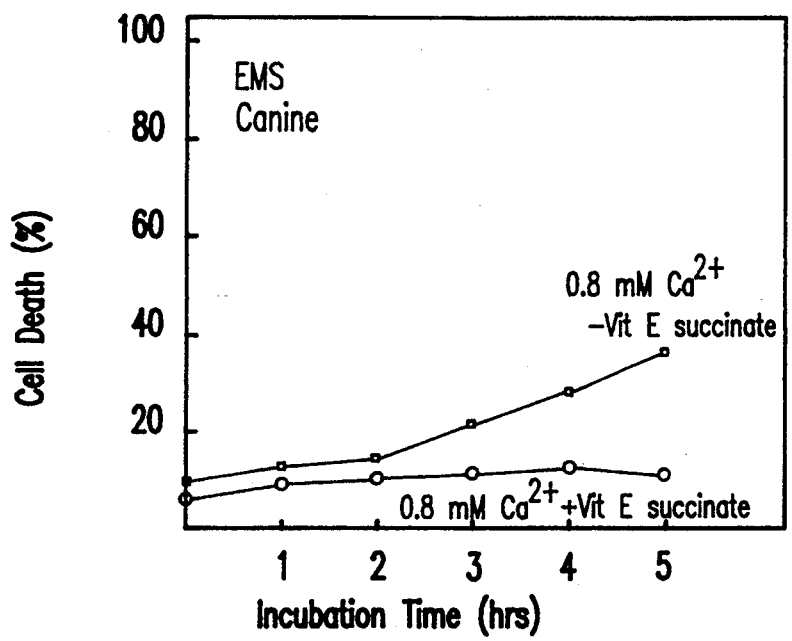
Figure 1D:
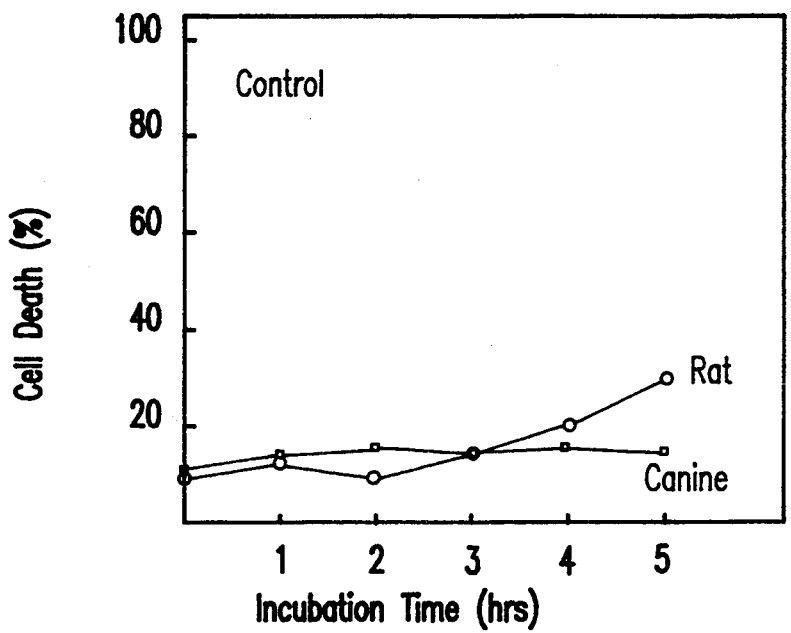

To determine if alpha-TS is a cytoprotective agent under physiological conditions, liver cells were incubated with Waymouth's medium containing approximately 1 mM extracellular $Ca^{2+}$ in the presence and absence of alpha-TS. FIGS. 1a and 1b show that 25 μM alpha-TS protected both rat and canine hepatocytes from the lethal effects of 50 mM of the alkylating agent ethylmethanesulfonate (EMS). FIG. 1c shows that 25 μM alpha-TS protected rat hepatocytes from the lethal effects of 5 μM of the ionophore A23187. FIG. 1d shows the response of control hepatocytes over the same period of time. The response curves shown in FIGS. 1a through 1c demonstrate alpha-TS is cytoprotective under physiological conditions and its anticytotoxic properties are not limited to a particular animal species. The protective effect of alpha-TS is retained in the water soluble polyethylene glycol (PEG) polymer of alpha-TS. When 25 μM of d-alpha-tocopheryl polyethylene glycol 1,000 succinate, available from Eastman Chemical Products, Inc. of Tennessee, was administered to rat hepatocytes, protection was observed against EMS-induced toxicity.

Figure 2A:
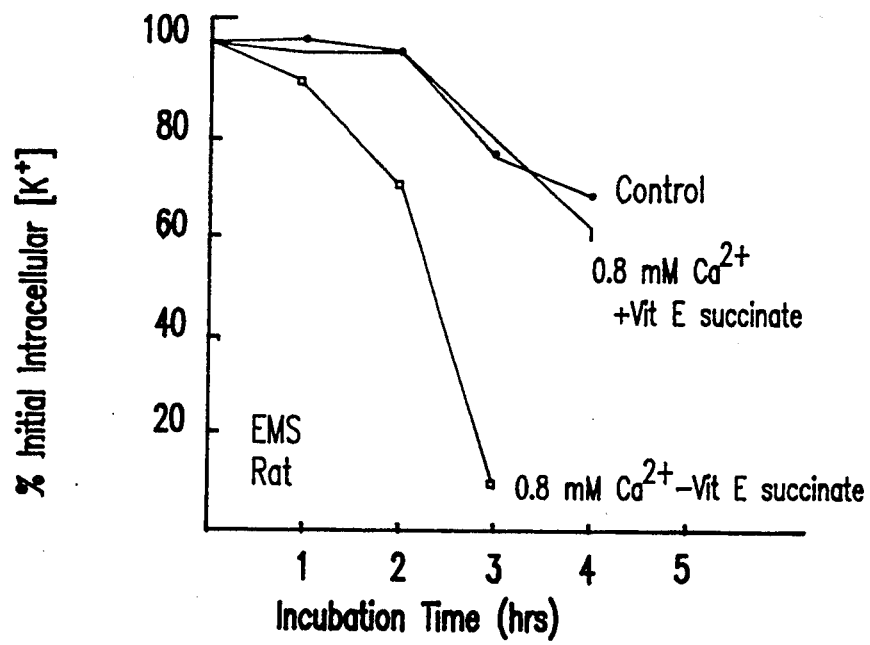
FIGS. 2a–2b are graphs showing the protective effect of alpha-TS on liver cell metabolic performance during a toxic insult.
Figure 2B:
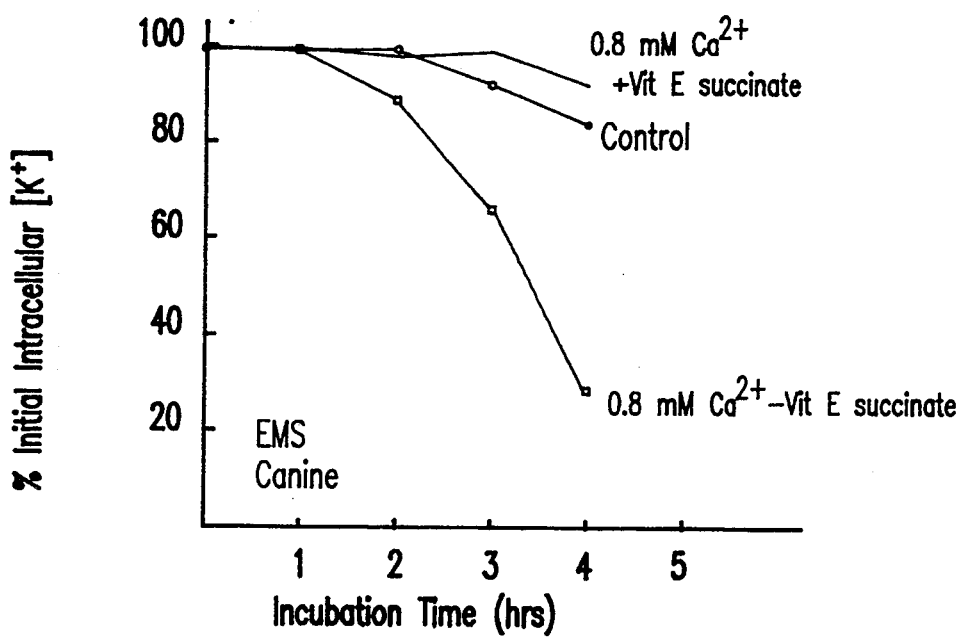

Medzhradsky, *Biochem. Med.* 13:164 (1975), has noted that the cell's ability to maintain its intracellular concentration of potassium ($K^+$) is an excellent indicator of the metabolic integrity of the cell. A concentration gradient exists for $K^+$ with greater concentrations found intracellularly. To maintain this gradient, the cell is dependent on the action of the $Na^+$-$K^+$ ATPase pump and an adequate supply of ATP. As cellular ATP levels decline, the ATPase pump is unable to maintain the gradient resulting in the loss of intracellular K+ by equilibration with the extracellular space. Because the maintenance of cellular metabolic processes is essential to the continual repair and survival of cells, organ systems, and organisms, the effect of alpha-TS on the metabolic integrity of rat liver cells during a toxic insult was investigated by measuring intracellular K+ levels. FIGS. 2a–2b show the response of rat and canine hepatocytes, respectively, exposed to 50 mM EMS. The cellular K+ concentration in untreated rat and canine hepatocytes declines rapidly, suggesting drug-induced injury and loss of metabolic performance. In contrast, rat and canine hepatocytes treated with 25µM alpha-TS during the toxic insult showed no loss of intracellular K+ as compared with control. The response curves shown in FIGS. 2a and 2b indicate that alpha-TS under physiological conditions can maintain the metabolic integrity of animal hepatocytes during a toxic insult.

Experiments were conducted in vitro to compare the protective effect of d-alpha-tocopherol (alpha-T), d-alpha-tocopherol acetate (alpha-TA), and alpha-TS on cells treated with a lethal dose of EMS. Table 2 shows the results of the experiments where rat liver hepatocytes were treated with 50mM EMS.

TABLE 2

Protective Effect of Tocopherol Analogs on Chemical Induced Toxicity and Lipid Peroxidation in Rat Liver Hepatocyte Suspensions

|   | Control | alpha-T | alpha-TA | alpha-TS |
|---|---|---|---|---|
| 1) % Protection | 0% | 19% | 12% | 100% |
| 2) % Inhibition of Lipid Peroxidation | 0% | 9% | 14% | 100% |
| 4) Cellular alpha-T(nmoles/$10^6$ cells) | 0.1 | 2.6 | 0.3 | 0.7 |
| 5) Cellular Tocopherol ester (nmoles/$10^6$ cells) | N.D. | N.D. | 1.7 | 2.6 |

Freshly isolated hepatocyte suspensions were prepared in medium with Waymouths medium and incubated with vitamin E (25µM, alpha-TS, alpha-T or alpha-TA) for approximately fifteen minutes. Suspensions were then treated with a toxic chemical (EMS, 50 mM; or ionphore A-23187, 5 µM) or a vehicle control and monitored hourly for loss of viability and cellular alpha-T, alpha-TS and alpha-TA content. At each time-point, rapid separation of viable from non-viable hepatocytes and medium was accomplished by the dibutyl phthalate centrifugation method. Cell viability was monitored hourly by measuring LDH leakage with a Cobas Analyzer and intracellular [K+] with a flame photometer. LDH was routinely measured in the medium while intracellular K+ was measured in the 10% perchloric acid lysate of viable cells. Lipid peroxidation was determined by measuring TBA reactants in the medium. The measurement of alpha-T levels were obtained by adding 1 nmol of the internal standard delta-tocopherol, to samples of viable hepatocytes. The samples were diluted with 0.3 ml 1% ascorbate in 0.1 M SDS, 0.4 ml ethanol, sonicated and extracted once with 0.8 ml hexane. Next, the hexane extract was evaporated to dryness with $N_2$, the residue dissolved in 2.5% ascorbate in methanol (1 ml) and analyzed (100 µl) by high-performance liquid chromatograph (HPLC). Measurements of alpha-T were made on a Hewlett Packard 1084B chromatograph equipped with a McPherson 749 fluorescence detector (excitation, 210 nm; emission filter, 320 nm) and a Spherisorb ODS II column (250×4.6 mm, 5 micron; Alltech, Avondale, Pa.). The mobile phase, 95% MeOH was run isocratically and the HPLC retention times for delta and alpha-tocopherol were approximately eleven and sixteen minutes, respectively. Cellular concentrations of the tocopherol esters, alpha-TS and alpha-TA, were determined by measuring the amount of alpha-T in cellular extracts before and after base hydrolysis. Cellular extracts (MeOH) described in the previous paragraph were divided into two portions with one analyzed for alpha-T (as described above) and the second (0.5 ml) treated with 0.2 ml of 4 M KOH overnight. Following the addition of 0.2 ml 4 M HC1, the neutralized KOH-MeOH extracted with 0.8 ml hexane. The hexane extract was evaporated with $N_2$, reconstituted in 2.5% ascorbate in MeOH and analyzed for alpha-T with HPLC as described above. The release of alpha-T by base hydrolysis using the above method was directly proportional to the alpha-TA or alpha-TS concentration (over the concentration range of 0.1–10 nmol). A standard curve for each tocopherol congener was run with every assay. The oxidation of alpha-T during the hydrolysis and analysis was prevented by the addition of 2.5% ascorbate to the MeOH. The limit of detection for alpha-T and alpha-T esters in the methods described above are 0.05 and 0.1 nmol/$10^6$ cells, respectively. Only viable cells were monitored in the laboratory procedures. Neither alpha-T nor alpha-TA protected cells from EMS; however, alpha-TS completely protected hepatocytes from EMS toxicity.

In Prasad, Cancer Res. 42:550 (1982), the unique effect of alpha-TS on the growth and morphology of cultured tumor cells incubated under physiological conditions was attributed to the accumulation of cellular alpha-T from alpha-TS. However, the experimental results shown in Table 2 indicate that cellular protection does not correlate with the accumulation of alpha-T, but instead is dependent on the presence of cellular alpha-TS. For example, hepatocytes with markedly elevated levels of cellular alpha-T (2.6 nmol/$10^6$ cells, alpha-T treated) and cellular alpha-TA (1.7 nmol/$10^6$ cells, alpha-TA treated) were susceptible to chemical induced toxicity and lipid peroxidation. In contrast, liver cells that accumulated alpha-TS (2.6 nmol/$10^6$ cells) and a modest amount of alpha-T (0.7 nmol/$10^6$ cells) were completely protected from chemical toxicity. In addition to its cytoprotective property, alpha-TS exhibits a membrane stabilization property by preventing EMS induced lipid peroxidation. Neither alpha-T nor alpha-TA demonstrated this property. Phospholipids are the major structural building blocks of cell membrane. Cell injury caused by chemical or radiation treatment is generally accompanied by activation of phospholipases which break down the cell barriers. The results shown in Table 2 correspond to observations by Toivanen, Prost. Leuk. Med. 26:265 (1987), which suggested alpha-TS inhibits platelet phospholipase $A_2$ activity. The ionizable tocopheryl congener (alpha-TS) may stabilize membranes by interacting with the charged portion of the phospholipid molecule or by chelating free intracellular $Ca^{2+}$.

The in vivo effect of alpha-TS was tested by administering a lethal oral dose of carbon tetrachloride (CC14) to male Sprague-Dawley rats. Table 3 shows in vivo results for $CCl_4$ challenges to rat viability.

TABLE 3

Protective Effect of Tocopherol Analogs on Carbon Tetrachloride (CCl4) Induced Lethality in Rats

| Toco-pherol Analog Administered | Days Survived After CCl4 Treatment (gCCl4/kg) | | | | $LD_{50}$ |
|---|---|---|---|---|---|
| | 5.0 | 3.8 | 2.9 | 2.2 | |
| Control (Vehicle Only) | 2 | 2 | 3 | >7 | 2.5 |
| d-alpha-T (100 mg/kg, ip) | 2 | 2 | 2 | 3 | 1.5 |
| d-alpha-TA (100 mg/kg, ip) | 2 | 2 | 3 | >7 | 2.5 |
| d-alpha-TS (100 mg/kg, ip) | 2 | >7 | >7 | N.D. | 4.4 |
| d-alpha-TS (100 mg/kg, oral) | 2 | 2 | 3 | >7 | 2.5 |

$LD_{50}$-Dose is the CCl4 required for 50% lethality.
$LD_{50}$ estimation performed according to Bruce, Tox. Appl. Pharm., Vol. 15, pg 151 (1985).
N.D.-Not Determined In addition to the data shown in Table 3, the alpha-T group was also exposed to 1.7g CCl4/kg body weight and 1.3g CCl4/kg body weight. At 1.7g CCl4/kg, the rats survived three days. At 1.3g CCl4/kg, the rats survived greater than seven days. In the experiment described in Table 3, a single dose of alpha-TS dissolved in peanut oil:ethanol (3:2) was given to male Sprague-Dawley rats. The dose was given 24 hours prior to an orally administered CCl4 challenge dissolved in peanut oil. Two to nine animals were tested per treatment. The control group comprised rats pretreated with the vehicle only. Survival was monitored for at least 7 days after the toxic insult. Rats treated with the vehicle alone died within two days of a 2.9g/kg CCl4 or greater challenge. Alpha-TS treated rats survived more than 7 days after a 3.8g/kg CCl4 or less challenge. These results demonstrate that alpha-TS treatment in vivo protects rats from the lethal effects of CCl4. Table 3 shows that an intraperitoneal dose of alpha-TS is far more protective than alpha-T or alpha-TA. The estimated lethal dose, $LD_{50}$, from CCl4 was increased from less than 2.5 to 4.4 g/kg body weight with the administration of 100mg/kg alpha-TS (ip). Histopathology was performed on rats treated with CCl4 and it was determined that the liver was the only organ affected by a CCl4 challenge (e.g., the other tissues appeared normal). Cytoprotection against CCl4 lethality was not observed after an oral dose of alpha-TS (100 mg/kg), which is the only form alpha-TS is currently commercially available in for therapeutic and prophylactic use.

In vivo experiments were performed to determine if alpha-TS administration protects the liver from chemical toxicity. The liver is the target organ for CCl4. CCl4 is a hepatotoxic agent that induces centrilobular liver necrosis through its metabolism to free radicals. Male Sprague-Dawley rats were given an intraperitoneal dose (100 mg/kg) of a tocopherol analog 24 hours prior to a CCl4 challenge (2.9g/kg given by oral garage). Forty eight hours after the challenge, the rats were sacrificed and the levels of aspartate aminotransferase (AST) and alanine aminotransferase (ALT) were measured. Table 4 shows the AST and ALT levels which were measured.

TABLE 4

Liver Specific Enzyme Levels in Rat Plasma 48 Hours After CCl4 Administration

| Treatment | AST | ALT |
|---|---|---|
| Negative Control (no CCl4) | 69 ± 5 | 34 ± 3 |

TABLE 4-continued

Liver Specific Enzyme Levels in Rat Plasma 48 Hours After CCl4 Administration

| Treatment | AST | ALT |
|---|---|---|
| Positive Control (CCl4) | 15,601 ± 5114 | 2,819 ± 1654 |
| d-alpha T + CCl4 | 17,330 ± 7220 | 4,678 ± 290 |
| d-alpha TA + CCl4 | 20,233 ± 3525 | 6,108 ± 417 |
| d-alpha TS + CCl4 | 3,430 ± 1500* | 631 ± 17* |

AST and ALT levels are listed in Units/L and expressed as X ± S.E. (n = 3–4).
*p < .05, as compared to other CCl4 treatments.

AST is the same enzyme as Serum Glutamic Oxalacetic Transaminase (SGOT) and ALT is the same enzyme as Serum Glutamic Pyruvate Transaminase (SGPT). AST and ALT levels are commonly used experimentally and clinically as indicators of liver cell injury or death. Alpha-TS pretreated rats had much lower AST and ALT levels than the alpha-T and alpha-TA pretreated rats. Liver histopathology from the experiment revealed that alpha-TS significantly reduced CCl4 induced centrilobular necrosis. In fact, seven to nine days following a 2.9g/kg CCl4 challenge the livers from rats pretreated with alpha-TS showed no histological signs of cell injury or cell death. These data indicate that the cellular accumulation of alpha-TS limits CCl4 destruction of the liver as well as promoting hepatic repair.

In vivo experiments were performed to determine the accumulation of alpha-T and esters of alpha-T in the liver. 100 mg/kg body weight of a tocopherol analog was administered to Sprague-Dawley rats using a peanut oil:ethanol vehicle (3:2). Twenty four hours later the rats were sacrificed and the accumulation of the tocopherol analog in the liver was determined. Table 5 contrasts the accumulation of alpha-T, alpha-TA, and alpha-TS (ip and oral).

TABLE 5

Concentration of Alpha-Tocopherol and Alpha-Tocopherol Ester in Rat Liver 24 Hours after Tocopherol Analog Administration in vivo

| Tocopherol Analog | Liver Concentration | | Protection from CCl4 |
|---|---|---|---|
| | Alpha-T | Ester | |
| Control (vehicle) | 28 ± 3 | N.D. | — |
| Alpha-T (ip) | 128 ± 10 | N.D. | No |
| Alpha-TA (ip) | 56 ± 10 | 92 ± 6 (alpha-TA) | No |
| Alpha-TS (ip) | 51 ± 5 | 119 ± 16 (alpha-TS) | Yes |
| Alpha-TS (oral) | 66 ± 12 | N.D. | No |

Alpha-T and Ester are in nmoles/g.
N.D.-Not Determined

The results of the experiment show alpha-TS cytoprotection is dependent on the cellular accumulation of the alpha-TS molecule, not on the accumulation of alpha-T. The most striking example of this dependency is the elimination of both the accumulation of hepatic alpha-TS and protection against CCl4 lethality when alpha-TS is administered orally. Presumably hydrolysis of the alpha-TS molecule occurred by duodenal esterases from biliary and pancreatic secretions.

In a one month study with three human males aging from 35 to 62 years 400 units of alpha-tocopheryl succinate were taken per day. Subsequent blood samples were taken from each individual and analyzed for alpha-T and alpha-TS content. Substantial amounts of alpha-TS in plasma and erythrocytes were observed for only one individual. Interpreting these results with the rat data shown in Table 5, it can be said that in the majority of the population, oral administration of alpha-TS will not result in the accumulation of tissue alpha- TS. However, in select individuals, as determined possibly by ethnic origin or diet, tissue alpha-TS accumulation can occur with oral dosing. The absence of alpha-TS hydrolysis in the gut of the one individual in the study who had substantial amounts of alpha-TS in plasma may be attributed to the absence of duodenal secretions after oral alpha-TS administration (lack of dietary fats to stimulate duodenal secretions at the time of alpha-TS administration).

A similar in vivo experiment to that discussed in conjunction with Table 5 was performed to determine if other tissues accumulate alpha-TS. Male Sprague-Dawley rats were given a 100 mg/kg dose of alpha-TS using a variety of chemical forms and vehicles. A variety of techniques were used to administer the alpha-TS. Twenty four hours later the rats were sacrificed and the tissues were tested for alpha-TS accumulation. Table 6 shows the accumulation of alpha-TS in each of the tissues tested during the experiment.

TABLE 6

Tissue Distribution of Alpha-Tocopherol and Alpha-Tocopherol Succinate 24 Hours After a 100 mg/kg Dose of Alpha-Tocopherol Succinate

| | | |
|---|---|---|
| (a) | Vehicle control | (No Alpha-TS) (1 dose) |
| (b) | Alpha-TS (ip) | (Alpha-TS dissolved in peanut oil and ETOH) (1 dose) |
| (c) | Alpha-TS (ip) | (K + salt of Alpha-TS dissolved in saline) (1 dose) |
| (d) | Alpha-TS (iv) | (K + salt of Alpha-TS dissolved in saline) (1 dose) |
| (e) | Alpha-TS (iv) | (Alpha-TS incorporated in liposomes) (1 dose) |
| (f) | Alpha-TS (ip) | (Alpha-TS in olive oil) (7 doses administered 1 per day for 7 days) |

| | | nmoles/gm of Tissue | | | | | |
|---|---|---|---|---|---|---|---|
| | | Liver | Brain | Kidney | Heart | Lung | Blood | Plasma |
| (a) | A-T | 28 | 27 | 29 | 27 | 47 | 10 | 13 |
| | A-TS | ND | ND | ND | ND | ND | ND | ND |
| (b) | A-T | 51 | 34 | 37 | 31 | 42 | 13 | 14 |
| | A-TS | 119 | ND | 31 | 47 | 90 | 7 | 8 |
| (c) | A-T | 260 | 37 | 45 | 48 | 93 | 21 | 22 |
| | A-TS | 518 | ND | 15 | 18 | 60 | 19 | 24 |
| (d) | A-T | 380 | 40 | 60 | 51 | 102 | 24 | 34 |
| | A-TS | 445 | ND | 27 | 24 | 385 | 18 | 30 |
| (e) | A-T | 105 | 47 | 52 | 68 | 112 | 22 | 26 |
| | A-TS | 322 | ND | ND | 10 | 4843 | 6 | 5 |
| (f) | A-T | 121 | 30 | 48 | 41 | 89 | 21 | — |
| | A-TS | 161 | 6 | 44 | 34 | 128 | 15 | — |

N.D.-Not Detected (Detection limit for Alpha-TS was 5-10 nmol/gm of Tissue)

The lung, kidney, heart, erythrocytes and plasma accumulate significant amounts of alpha-TS when administered intraperitonealy (ip) or intravenously (iv). By changing the chemical form (K+ salt) or vehicles (liposomes), the accumulation of alpha-TS can be targeted towards specific tissues. Repeated administration, (f) in table 6, resulted in accumulation of alpha-TS in the central nervous system. Note that the results in Table 6 were determined twenty four hours after a single dose of alpha-TS. Additional tests revealed that alpha-TS could not be detected forty eight hours after a single dose administration of alpha-TS.

The data in Table 6 suggest that protection following alpha-TS administration would not be specific to one organ or tissue type. An in vivo experiment with Sprague-Dawley rats confirmed this assumption. Rats received a 100 mg/kg (ip) dose of alpha-TS twenty four hours prior to a 40 mg/kg (ip) insult of paraquat which is a lung specific toxic agent. The rats also received a 100 mg/kg (ip) dose of alpha-TS each day after the paraquat insult. Protection with alpha-TS administration was observed by its ability to extend the survival time of the paraquat exposed rats from 4 days to 6 days. In addition to the paraquat results, rats pretreated with alpha-TS prior to a toxic dose of $CCl_4$ recover from the acute central nervous system toxic manifestations of $CCl_4$, which include CNS depression resulting in narcosis, several days before rats which are not treated with alpha-TS. Hence, alpha-TS protects rats from neurotoxic as well as hepatotoxic effects of $CCl_4$.

In vivo experiments were performed to determine if the time the ionizable tocopherol analog (alpha-TS) is administered affects the cytoprotective functions. Male Sprague-Dawley rats were given a 100 mg/kg intraperitoneal dose of a tocopherol or succinate analog and were given a lethal dose of $CCl_4$ (2.9g/kg by oral gavage). Table 7 contrasts the times of administration of the tocopherol or succinate analog and the times of administration of the lethal dose of $CCl_4$ with the survival of the rats in the study (3 to 6 rats per protective treatment).

TABLE 7

Protective effect of Tocopherol and Succinate Analogs on $CCl_4$ Induced Lethality in Rats

| | Tocopherol Analog Administered | Days Survived after $CCl_4$ |
|---|---|---|
| 1. | Vehicle Control | 2 |
| 2. | Alpha-TS (100 mg/kg, single dose 24 hours prior to $CCl_4$) | >7* |
| 3. | Alpha-TS (100 mg/kg, single dose 12, 10, 8, 6, 4, 2, or 1 hour prior to $CCl_4$) | 2 to 4 |
| 4. | Alpha-TS (100 mg/kg, dosed 1 hour prior to $CCl_4$ and daily thereafter) | >7* |
| 5. | Alpha-TS (100 mg/kg, dosed 1 hour after $CCl_4$ and daily thereafter) | 2 |
| 6. | Succinic Acid, Na Salt (1 g/kg, dosed 24 hours or 1 hour prior to $CCl_4$ and daily thereafter) | 2 |
| 7. | Monomethyl Succinate (1 g/kg, dosed 24 hours and 1 hour prior to $CCl_4$) | 2 |
| 8. | Dimethyl Succinate (1 g/kg, dosed 24 and 1 hour prior to $CCl_4$) | 2 |

*$p < .05$, as compared to vehicle control

Table 7 shows that greater than 12 hours of incubation time are required for cytoprotection if a single dose of alpha-TS is used. However, the incubation time required after alpha-TS administration can be reduced to one hour if daily injections of alpha-TS are given after the $CCl_4$ insult. Based on the fact that a single dose of alpha-TS leaves the system after forty eight hours, the optimal dosing would be periodic (daily). The results suggest that optimal cytoprotection results from daily or multiple dosing of alpha-TS. The finding that alpha-TS did not protect cells after a $CCl_4$ challenge may suggest that alpha-TS should be given in advance, i.e., take alpha-TS before an X-ray examination, or heart surgery. Alpha-TS treatment after the toxic challenge may still be effective if milder challenges are applied. Table 7 shows that succinic acid, monomethyl succinate and dimethyl succinate are not cytoprotective.

In vitro experiments were performed to determine if alpha-TS could protect cells from different toxic insults. Under physiological conditions, rat hepatocytes were incubated with medium containing 25 $\mu$M alpha-TS. The hepatocytes were exposed to EMS, a potent mutagen and alkylating agent; the ionophore A23187, a membrane active compound that permits the equilibration of divalent cations across cell membranes; cadmium, a heavy metal, environmental contaminant, and known carcinogen who's mechanism of toxicity remains unknown; 95% $O_2$, an excessive oxygen insult that produces an abundance of toxic oxygen free radicals and reactive oxygen intermediates in the cell; doxorubicin (adriamycin), a clinically important antitumor agent with cytotoxic effects proposed to result from its metabolic activation and the generation or reactive oxygen species; carbon tetrachloride ($CCl_4$); and hypoxia (an absence of oxygen followed by reoxygenation). Table 8 shows the results of the experiments.

TABLE 8

Protective Effect of d-Alpha-Tocopherol Succinate on Rat Hepatocytes Exposed to a Variety of Toxic Insults.

| Toxic Insults | % Cell Death | |
|---|---|---|
| | No Alpha-TS | Alpha-TS |
| Control (Vehicle only) | 21 | 21 |
| EMS (50 mM) | 68 | 25 |
| Ionophore A23187 (5 µM) | 73 | 24 |
| Cadmium (0.1 mM) | 70 | 24 |
| 95% Oxygen | 57 | 23 |
| Doxorubicin (100 µM) | 62 | 28 |
| $CCl_4$ (2.5 mM) | 63 | 38 |
| Hypoxia (accomplished by 4 hrs under $N_2$ and 2 hrs under $O_2$) | 70 | 49 |

Table 8 shows that 25 µM alpha-TS protects (note control) rat hepatocytes from lethal doses of EMS, Ionophore A23187, Cadium, Oxygen, Doxorubicin, $CCl_4$, and hypoxia.

In vivo experiments were performed to determine if alpha-TS administration protects the liver from the hepatotoxic effects of acetaminophen. Acetaminophen is a commonly used analgesic that is metabolized to a reactive intermediate. One group of male Sprague-Dawley rats were given an intraperitoneal dose (100 mg/kg) of alpha-TS 24 hours prior to an acetaminophen challenge (2.5 g/kg body weight given by oral gavage). The other group of male Sprague-Dawley rats received only the acetaminophen challenge. Forty eight hours after the challenge the rats were sacrificed and the levels of aspartate aminotransferase (AST) and alanine aminotransferase (ALT) were measured. Table 9 shows the AST and ALT levels which were measured.

TABLE 9

Liver Specific Enzyme Levels in Rat Plasma 24 hours After Acetaminophen Administration

| Treatment | AST (Units/L) | ALT (Units/L) |
|---|---|---|
| Vehicle Only (20% Tween 80) | 67 ± 8 | 49 ± 6 |
| Acetaminophen (ACT) | 6,968 ± 3546 | 2,137 ± 442 |
| (ACT) + alpha-TS | 1,659 ± 607 | 432 ± 188* |

*$P < .05$, as compared to other ACT treatments

Table 9 shows that pretreating rats with alpha-TS greatly suppresses the damage associated with free radical production by acetaminophen.

Figure 3:
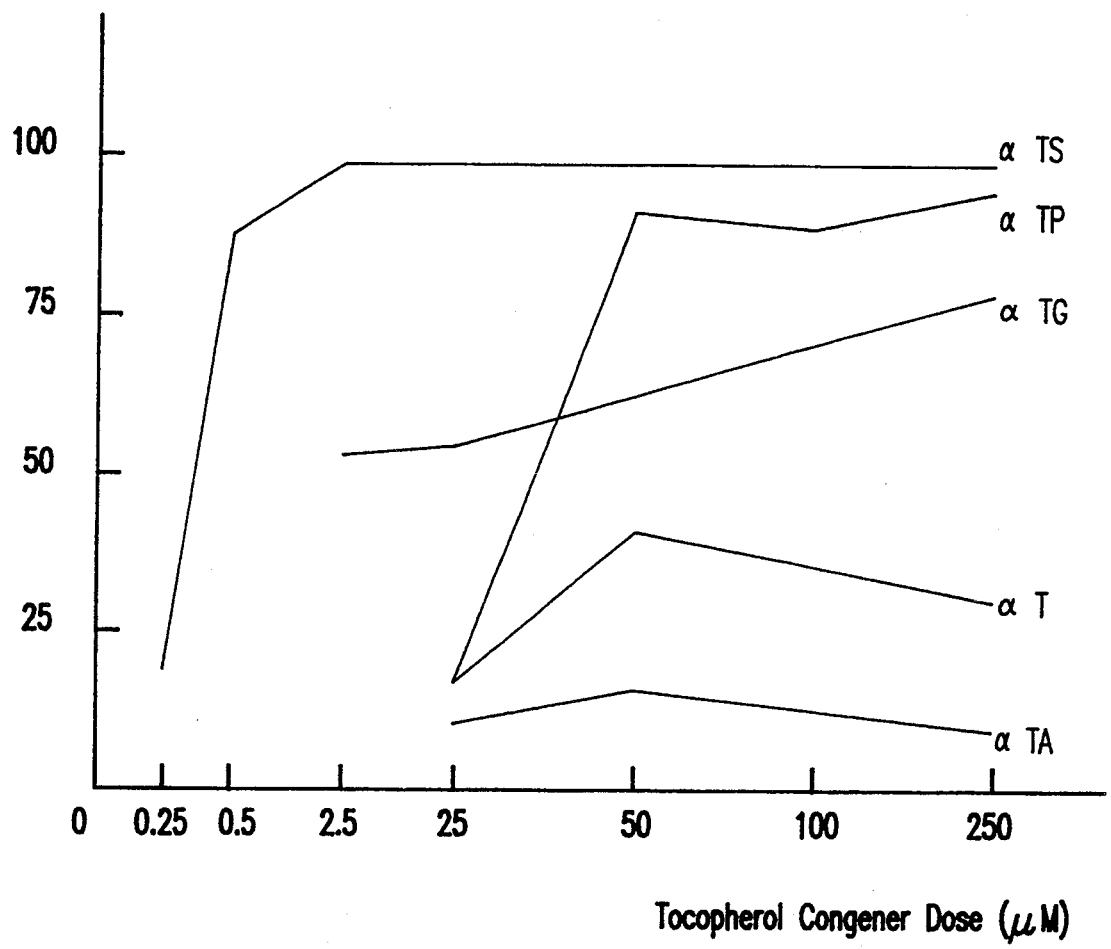
FIG. 3 is a graph showing the dose response of tocopherol congeners for protection of hepatocytes from EMS toxicity.

To determine the relative cytoprotective potency of various tocopherol derivatives, the effect of varying doses of a tocopherol analog on the protection against EMS-induced toxicity was examined in vitro on rat hepatocyte suspensions. Specifically, the following ionizable tocopherol congeners were tested: alpha-TS, alpha tocopheryl glutarate (alpha-TG), and alpha tocopheryl phosphate (alpha-TP). FIG. 3 shows a graphical representation of the percentage cytoprotection achieved with varying doses of the tocopherol derivatives. The response of varying quantities of alpha-T and alpha-TA are also represented on FIG. 3. Alpha-TS has the greatest potency with 100% protection against the loss of viability and metabolic performance observed at concentrations as low as 2µM. At 2µM, the cellular alpha-TS content was approximately 0.1 nmoles/$10^6$ cells or 10 nmoles/gram of tissue. With 0.5µM alpha-TS, substantial (85%) protection against loss of viability was observed. At 0.5µM, the cellular alpha-TS content is approximately 0.025nmoles/$10^6$ cells. 0.1 nmoles is the lower detection limit. Since there are approximately $10^8$ cells per gram of tissue, cytoprotection can be afforded by administering an appropriate amount of alpha-TS to a patient to achieve a 2.5 nmoles/gram concentration. Protection was not afforded hepatocytes incubated with alpha-T or alpha-TA at concentrations up to 250 µM. Significant protection against EMS toxicity was observed at alpha-TP medium concentrations of 50 µM and above. Possible explanations for the difference in potency observed between alpha-TS and alpha-TP are that the latter derivative was administered as water soluble salts in saline.

To confirm the cytoprotective properties of alpha-TP under physiological conditions in vitro tests using primary cultures of adult rat hepatocytes were conducted (another in vitro model system). Unlike the hepatocyte suspensions used for the in vitro modeling discussed above, cultured hepatocytes retain their in vivo cuboidal shape as a result of attachment to a collagen matrix, and their lifespan in vitro is 5 to 7 days, instead of 8–12 hours (as with suspensions). Table 10 shows the percentage cell death observed and the lipid peroxidation as measured by malondialdehyde (MDA) production observed with varying concentrations of the disodium salt of alpha-TP.

TABLE 10

Protective Effect of dl-Alpha-Tocopheryl Phosphate on Chemical Induced Toxicity and Lipid Peroxidation in Cultured Rat Hepatocytes.

| Incubation Conditions (6 hrs.) | | Cell Death (%) | Lipid Peroxidation |
|---|---|---|---|
| Negative Control (Vehicle Only) | | 10 ± 1 | 2.3 ± 0.3 |
| Positive Control (50 mM EMS Only) | | 61 ± 8 | 9.4 ± 1.1 |
| EMS + dl-alpha-TP | 25 µM | 16 ± 3 | 2.5 ± 0.9 |
| | 100 µM | 15 ± 3 | 2.3 ± 0.1 |
| | 250 µM | 20 ± 3 | 1.7 ± 0.1 |

Lipid peroxidation reported as µmoles MDA/$10^6$ cells

Table 10 shows that cultured hepatocytes are completely protected from the toxic effects of EMS by alpha-TP ($\geq 25$ M). Furthermore, alpha-TP treatment also prevented EMS-induced lipid peroxidation. These results are similar to those observed in hepatocyte suspensions for both alpha-TS and alpha-TP, and indicate that alpha-TP, like alpha-TS is indeed a potent cytoprotective agent with unique anticytotoxic properties. Interestingly, like alpha-TS, alpha-TP mediated cytoprotection is eliminated by increasing the extracellular $Ca^{2+}$ concentration to 3.5 mM from the physiological conditions of approximately 1mM.

Alpha-TS has been found to be beneficial for tissue injury repair in human beings. In one case, the middle knuckle of the left hand of a 42 year old woman was injured by the removal of a small wart with liquid nitrogen. Two months following the liquid nitrogen insult, the injured area (approximately 1 cm in diameter) was characterized by scar tissue raised several millimeters above the surrounding normal skin. At this time, the lesion was treated by wetting the injured area with alpha-TS dissolved in dimethyl sulfoxide (100mg/ml), daily for a period of two weeks. This treatment resulted in the rapid healing of the injured area with the elimination of scar tissue. One year following the last alpha-TS treatment, the once injured area remains indistinguishable from the surrounding normal tissue. In another case, a 42 year old woman's lip was severely sunburned. Topical lip cremes and antibiotic cremes were used for several weeks following the ultraviolet insult with minimal therapeutic benefit. At this time, the lesion was treated by wetting the injured area with alpha-TS dissolved in dimethyl sulfoxide (100mg/ml) daily for a period of 1 week. This treatment resulted in the rapid healing of the lip without scar formation. In another case, the arch of the left foot of a 42 year old woman was inflamed and blistered from contact dermatitis or stress dermatitis. Six months after unsuccessful treatment on this lesion with betamethasone, the injured area was treated by wetting the injured area with alpha-TS dissolved in dimethyl sulfoxide (100 mg/ml) twice daily for a period of 1 week. This treatment resulted in the rapid healing of the foot lesion with the dissolution of both inflammation and blisters. Since dimethyl sulfoxide does not affect wound healing (See Goldblum, *Proc. Soc. Exper. Biol. Med=*, 172:301, (1983)) the cases described above suggest that alpha-TS applied topically is beneficial in repairing dermal injuries from a variety of insults. It is also evident from these cases that alpha-TS is the active component that promotes wound healing and prevents scar formation.

The above studies prove an intact ionizable tocopheryl congener (such as alpha-TS or alpha-TP) is required for cytoprotection. Protecting the ionizable tocopheryl congener from hydrolysis and esterase activity may be a critical concern during administration. The experimental results show that intravenous, intraperitoneal and dermal routes allow cellular accumulation of the intact ionizable tocopheryl congener. Other routes that would be effective for the cellular delivery of an ionizable tocopheryl congener would include subcutaneous injection, intramuscular injection, intrathecal injection, ocular administration (eye drops), sublingual administration, nasal spray administration, transdermal administration (with transdermal patches), and rectal administration (suppository). Coating the cytoprotective molecule with an impermeable polymer membrane that is not susceptible to the action of digestive enzymes (duodenal esterases) or is biodegraded very slowly should allow the ionizable tocopheryl congener to be taken orally (See, Safran et al., *Science* 233:1081 (1986) and Damage et al., *Diabetes* 37:246 (1988) for a discussion of protective coatings). In addition, amino acid polymers such as polylysine could be used. Impermeable polymer films would be degraded by microflora found in the colon. Thus, the ionizable tocopheryl congener contained therein would be released in a part of the intestine devoid of secreted digestive enzymes.

Release of alpha-tocopherol from the ionizable tocopheryl congener is probably not responsible for the observed cytoprotection. Varying concentrations of alpha-T and alpha-TS were used to pretreat rat hepatocytes. The hepatocytes were subsequently exposed to 50mM EMS for three hours. Table 11 presents the concentrations of alpha-T and alpha-TA as well as the protection from toxic injury observed.

TABLE 11

Effect of Tocopherol Analog Dose on the Concentration of Alpha-T and Alpha-TS and on Cytoprotection in Rat Hepatocytes Exposed to EMS for 3 Hours

| Treatment | | Hepatocyte Concentration[a] in nmol/$10^6$ cells | | Protection From Toxic Injury |
|---|---|---|---|---|
| | | Alpha-T | Alpha-TS | |
| Control | | 0.2 ± 0.1 | N.D. | No |
| Alpha-T | 25 μM | 2.1 ± 0.7 | N.D. | No |
| | 50 μM | 6.1 ± 0.7 | N D. | No |
| | 250 μM | 23.7 ± 2.4 | N.D. | No |
| Alpha-TS | .5 μM | 0.2 ± 0.1 | N.D. | Yes |
| | 2.0 μM | 0.4 ± 0.1 | 0.2 ± 0.1 | Yes |
| | 10 μM | 0.8 ± 0.1 | 0.7 ± 0.1 | Yes |
| | 25 μM | 0.9 ± 0.1 | 2.5 ± 0.1 | Yes |
| | 250 μM | 0.9 ± 0.1 | 7.6 ± 1.7 | Yes |

[a] Expressed as X ± SEM, N = 3
N.D. — Not Detected. Limits of detection are 0.05 nmol/$10^6$ cells for alpha-T and 0.1 nmol/$10^6$ cells for alpha-TS The exposure of rat hepatocytes to high concentrations of alpha-tocopherol (250 μM) results in a greater than 100 fold increase in cellular alpha-tocopherol levels (23.7 nmol/$10^6$ cells); however, the cells are not protected against the EMS toxic insult. Cytoprotective concentrations of alpha-TS resulted in only a slight increase in the cellular alpha-tocopherol content. Therefore, it can be concluded that the cellular accumulation of alpha-T is not responsible for ionizable tocopheryl congener induced cytoprotection. Table 11 supports the proposition that cytoprotection may be in part derived from stabilization of the cellular membranes where the tocopherol portion interacts with the unsaturated fatty acid portion of phospholipids and the ionizable succinate portion interacts with the polar end of the membrane phospholipid molecule. To test this proposition, in vitro experiments have been conducted with alpha-TP and alpha-tocopheryl 3-methyl succinate (alpha-TMS). It was found that cytoprotection against EMS induced toxicity was characterized by a cellular accumulation of alpha-TP (2.68 nmols/$10^6$ cells) or alpha-TMS with a minimal release of cellular alpha-T (0 to 0.15 nmols/$10^6$ cells).

In vitro experiments were conducted with a variety of different tocopherol and succinate analogs to determine which were protective against EMS induced toxicity. After five hours of incubation with 50 mM EMS and 25μM of a tocopherol or succinate analog, cytoprotection was determined by comparing the percentage of LDH leakage from control hepatocytes (vehicle only, assumed 100% protection) with the EMS only treated cells (assumed 0% protection). The results shown in Table 12 are obtained from three to eight separate hepatocyte preparations.

TABLE 12

Protective Effect of Tocopherol and Succinate Analogs on EMS-Induced Toxicity in Rat Hepatocytes

| Administered Tocopherol or Succinate Analog (25 μM) | Percent Cytoprotection |
|---|---|
| Vehicle Control | 100 ± 9 |
| EMS Only | 0 ± 17 |
| Alpha-Tocopherol | 8 ± 10 |
| Alpha-Tocopherol + Succinic Acid | 26 ± 3 |
| Succinic Acid | 0 ± 23 |
| Alpha-Tocopherol Succinate | 92 ± 3* |
| Alpha-Tocopherol Succinate, K+ Salt | 97 ± 3* |
| Alpha-Tocopherol Succinate Polyethylene Glycol (PEG) Ester | 80 ± 15* |
| Alpha-Tocopherol 3-Methyl Succinate | 70 ± 9* |
| Alpha-Tocopherol Succinate Methyl Ester | 22 ± 15 |

TABLE 12-continued

Protective Effect of Tocopherol and Succinate
Analogs on EMS-Induced Toxicity in Rat Hepatocytes

| Administered Tocopherol or Succinate Analog (25 μM) | Percent Cytoprotection |
|---|---|
| Alpha-Tocopherol Succinamide | 0 ± 11 |
| Alpha-Tocopherol Glutarate | 55 ± 15* |
| Delta-Tocopherol Succinate | 70 ± 24* |
| Delta-Tocopherol | 0 ± 11 |
| Cholesteryl Succinate | 30 ± 22 |
| Cholesterol | 30 ± 16 |

*P < .05, as compared to EMS only treatment group

Table 12 shows that 25μM of an ionizable tocopheryl congener (alpha-TS, K+ salt of alpha-TS, alpha-TG, PEG ester of alpha-TS, and delta-TS) were protective against 50 mM EMS-induced toxicity in vitro. If the ionic nature of the congener is altered (i.e., methyl ester of alpha-TS or alpha-tocopheryl succinamide) the cytoprotective properties are diminished or eliminated. Alpha-tocopherol monoglutarate was prepared by the following synthesis. To 2.3g (5.3 nM) of alpha-tocopherol was added 1.4g (12.4 nM) of glutaric anhydride and 0.123g (0.89 nM) of anhydrous potassium carbonate. The mixture was stirred and heated at 150°–160° for four hours. The mixture was cooled, dissolved in chloroform and passed through a silica column for purification. Of the twenty fractions which were collected, fractions ten through sixteen contained 3.0g of the desired alpha-tocopherol mono glutarate. The presence of alpha-tocopherol monoglutarate was confirmed by TLC, NMR, and HPLC. TLC showed Rf=0.47 (chloroform-methanol 9:1)(By comparison with alpha- tocopherol mono succinate which has and Rf=0.33 in chloroform-methanol 9:1). NMR showed no aromatic protons, the protons of the carboxylic acid showed a broad peak at 4.5–5.8, the three —$CH_2$—(alkyl) groups of the glutaric acid showed multiplets and triplets at 2.4 and 2.9, the remaining peaks of the NMR are similar to those shown by alpha-tocopherol itself. HPLC showed base hydrolysis liberating greater than 95% of the expected concentration of alpha-tocopherol. Alpha tocopherol-3-methyl succinate was prepared by using the same molar quantities of reactants and catalysts as used in the alpha-tocopherol monoglutarate preparation except methylsuccinic anhydride was used in place of the glutaric anhydride. Heating temperatures and times as well as purification were similar. The presence of alpha-tocopherol 3-methyl-succinate was confirmed by TLC, NMR, and HPLC. TLC showed Rf=0.33 in chloroform-methanol 9:1. NMR showed no aromatic protons, the proton of the carboxylic acid group showed a very broad peak between 5 and 7, the remaining peaks are very similar to alpha-tocopherol monosuccinate with major peaks as follows: a doublet at 0.85, a multiplet at 1.0–2.6, a triplet at 1.6–1.9, a multipier at 1.9–2.2, and a multipier at 2.2–3.5. HPLC base hydrolysis liberated greater than 95% of the expected concentration of alpha-tocopherol. Delta-tocopherol mono succinate was prepared by using the same molar quantities of reactants and catalysts as used in the alpha-tocopherol mono glutarate preparation except delta tocopherol was used in place of alpha tocopherol and succinic anhydride was used in place of glutaric anhydride. Heating temperatures and times as well as purification were similar. The presence of delta-tocopherol mono succinate was confirmed by TLC, NMR, and HPLC. TLC showed Rf=0.37 in chloroform:methanol 9:1. NMR showed two aromatic protons at 6.65 and at 7.35. The proton of the carboxylic acid group spread widely. The main peaks are a doublet at 0.85, a multiplet at 1.0–2.0, a singlet at 1.15, and a multiplet at 2.5–3.0. HPLC base hydrolysis liberated greater than 95% of the expected concentration of delta-tocopherol.

FIGS. 4a and 4b show the structure versus activity correlation between the chemical nature of a tocopheryl congener and its cytoprotective potency (as derived from the in vitro results indicated in Table 12). From FIGS. 4a and 4b it can be concluded that cytoprotection may be related to the ionic nature of the ester congener. Optimal cytoprotection is observed when the ionic nature of the ester functional group (i.e. succinate) is maintained following attachment to tocopherol. By eliminating the ester (e.g., alpha-T) or the ionic nature of this functional group after esterification with tocopherol (e.g., alpha-TA, methyl ester of alpha-TS, or alpha-T succinamide) cytoprotective properties of the compound are dramatically reduced. Ionizable functional groups include the following anions: hydroxyls, carboxylic acids, sulfates, phosphates, thiols and selenic acids, and the following cations: amines.

An in vitro experiment with rat hepatocyte suspensions was performed to determine the effect of esterase inhibitors on alpha-TS. Table 13 shows the percentage of cell death resulting from treating the hepatocytes with 50 mM EMS and with two potent esterase inhibitors, diethyl-p-nitrophenyl phosphate (DENP) and Bis-(p-nitrophenyl) phosphate (BNPP).

TABLE 13

Effect of Esterase Inhibitors on Alpha-TS Mediated Protection in Hepatocyte Suspensions Exposed to EMS
(1) 50 mM EMS (2) 25 μM alpha-TS
(3) 100 μM Diethyl p-nitrophenyl phosphate
(4) 100 μM Bis-(p-nitrophenyl) phosphate

| Incubation conditions | Cell Death (%) | % Initial Intra-cellular [K+] | nmoles/$10^6$ cells Cellular alpha-T | Cellular alpha-TS |
|---|---|---|---|---|
| Control | 26 ± 4 | 93 ± 9 | .26 ± .05 | N.D. |
| (1) | 61 ± 5 | 27 ± 13 | .18 ± .05 | N.D. |
| (1) + (2) | 30 ± 7* | 93 ± 11* | .81 ± .05* | 2.73 ± .67 |
| (1) + (2) + (3) | 58 ± 8 | 26 ± 2 | .19 ± .05 | 2.56 ± .24 |
| (1) + (2) + (4) | 52 ± 3 | 14 ± 6 | .20 ± .05 | 2.61 ± .61 |

N.D. — not detected.
*P ≤ 0.01, n = 3; as compared to EMS treatment.

As expected from the earlier experiments, alpha-TS administration protected hepatocytes against EMS-induced cell injury and death. However, when cells were pretreated with an esterase inhibitor prior to alpha-TS administration and EMS exposure, the protective effect of alpha-TS and the release of alpha-tocopherol were abolished. These data suggest that by preventing the release of alpha-tocopherol and succinate from alpha-TS, the cytoprotective properties of alpha-TS can be reduced. Because previous experiments demonstrated that cellular alpha-T accumulation is not cytoprotective, these data indicate that the cellular release of succinate from alpha-TS may be partially responsible for alpha-TS mediated cytoprotection.

It is well known that the succinate molecule is utilized by the cell to produce ATP energy. In the tricarboxylic acid cycle, succinate is oxidized by succinate dehydrogenase to produce ATP. Oxidation occurs in the mitochondria and the mitochondria can utilize both succinate formed in the mitochondria or succinate transported to the mitochondria. Increasing ATP production may enhance cellular repair processes as well as normal metabolic processes. For example, the cell's ability to remove free intracellular $Ca^{2+}$ during a toxic insult is related to ATP production. Succinate administration stimulates gluconeogenesis to form glucose 6-phosphate which is used for producing energy anaerobically (ATP formation through glycolysis) and for producing reducing equivalents (NADPH formation through the hexose monophosphate shunt needed for lipid and nucleotide biosynthesis and other biosynthetic reductions and enzymatic reactions, e.g., glutathione reductase). An in vitro experiment was conducted to determine the relationship between the release of succinate from alpha-TS and the cellular ATP level. The experiment was performed by incubating a tocopherol analog in a rat hepatocyte suspension and measuring the ATP level at the beginning and end of the test. Table 14 shows the ATP levels measured for a six hour incubation.

TABLE 14

Effect of Tocopherol Analogs and Succinate on the ATP Content of Hepatocyte Suspensions During a 6 Hour Incubation

| Incubation Conditions | Cellular ATP (nmoles/$10^6$ cells) 0 Hr | 6 Hr | Rate of ATP Depletion in (nmoles/$10^6$ cell/hr) |
|---|---|---|---|
| Vehicle Control | 14.9 ± 1.6 | 5.0 ± 0.4 | 1.6 ± 0.2 |
| Alpha-TS | | | |
| 25 μM | 20.1 ± .5 | 14.2 ± 0.8* | 1.0 ± 0.1* |
| 250 μM | 15.2 ± 1.6 | 11.7 ± 2.0* | 0.6 ± 0.3* |
| Alpha-T | | | |
| 25 μM | 15.2 ± 1.6 | 6.3 ± 0.8 | 1.5 ± 0.2 |
| Alpha-TP | | | |
| 50 μM | 19.4 ± 1.6 | 7.3 ± 0.2 | 2.0 ± 0.2 |
| Succinate | | | |
| 25 μM | 15.7 ± 1.3 | 4.9 ± 0.6 | 1.8 ± 0.2 |

*P ≦ 0.05, n = 3; as compared to control

Control hepatocytes, which did not experience a toxic insult, lose approximately 65% of their endogenous ATP stores during a 6 hour incubation. Alpha-TS administration prevented rapid depletion of intracellular ATP. Succinate and alpha-tocopherol administration did not slow the depletion of intracellular ATP. Contrasting this data with that of Table 12, alpha-TS is cytoprotective and succinate and alpha-T are not. However, alpha-TP, which is cytoprotective, did not slow the depletion of intracellular ATP.

In vitro experiments have been conducted to determine the cytoprotective activity of succinate derivatives on EMS induced toxicity. Rat hepatocyte suspensions were subjected to 50 mM EMS and the percentage of cell death, the percentage of intracellular $K^+$ (a metabolic parameter as discussed above), the depletion of ATP and the effect on lipid peroxidation were monitored. Table 15 shows the results obtained for rat hepatocyte suspensions pretreated with different succinate derivatives.

TABLE 15

Effect of Succinate Derivatives on EMS induced Toxicity in Rat Hepatocyte Suspensions
(1) 50 mM EMS
(2) 25 μM alpha-TS
(3) 50 μM methyl ester of alpha-TS
(4) 100 μM Cholesteryl Succinate
(5) 250 μM Monomethyl Succinate
(6) 250 μM Dimethyl Succinate

| Incubation Conditions | Cell Death | % Initial Intracellular | Lipid Peroxidation |
|---|---|---|---|

TABLE 15-continued

| (5 Hrs) | (%) | [K+] | [ATP] | nmolMDA/$10^6$ cells |
|---|---|---|---|---|
| Vehicle only | 24 ± 1 | 94 ± 2 | 64 + 7 | 0.9 |
| (1) | 59 ± 1 | N.D. | N.D. | 14.4 |
| (1) + (2) | 27 ± 1** | 86 ± 6** | 45 ± 2** | 0.9 |
| (1) + (3) | 30 ± 1** | 67 ± 4** | — | — |
| (1) + (4) | 48 ± 4* | N.D. | — | 11.3 ± 4.2 |
| (1) + (5) | 61 ± 5 | N.D. | — | 12.8 ± 1.0 |
| (1) + (6) | 60 ± 1 | N.D. | — | 12.6 ± 0.2 |

N.D. — Not Detected
**P ≦ 0.01, n = 3; as compared to EMS treatment alone.
*P ≦ 0.05, n = 3; as compared to EMS treatment alone.

Treating hepatocytes with methyl esters of succinate did not provide the hepatocyte suspensions with protection from EMS induced injury, membrane lipid oxidation, or cell death. Concentrations as small as 25μM of alpha-TS provides cytoprotection while concentrations as high as 250μM of monomethyl succinate and dimethyl succinate were ineffective. Cytoprotection of the methyl ester of alpha-TS and cholestryl succinate appear to be dosage dependent (i.e., Table 15 shows the methyl ester of alpha-TS and cholesteryl succinate are cytoprotective at 50μM and 100μM, respectively, but Table 12 shows they are not cytoprotective at 25μM). The methyl ester of alpha-TS is also capable of the cellular release of alpha-tocopherol and succinate. The methyl ester of alpha-TS and alpha-tocopheryl succinamide have increased lipophilicity and may prove useful in promoting the accumulation of alpha-TS and cytoprotection in the central nervous system.

Alpha-TS may provide a transport system and cellular reservoir for succinate. Alpha-T is a lipophilic, membrane-bound cellular protective component. It is sequestered in virtually all cells and tissues and is membrane bound in virtually every subcellular organelle. The largest accumulation of alpha-T is found in the mitochondria, endoplasmic reticulum and nucleus. Simon et al., Fed. Proc. 16:249 (1957), reported that alpha-TS administration in vivo results in alpha-TS accumulation in the membranes of the endoplasmic reticulum and mitochondria. The inventors results in Table 6 show that alpha-TS accumulation is detectable in the liver, kidney, brain, heart, lung, blood and plasma. Alpha-T could transport the succinate ester into the cell, whereupon esterases hydrolyze the ester to separate alpha-T and succinate. The diminished protection observed in vitro for cholesteryl succinate administration, reported in Table 15, probably is a result of the insoluble nature of cholesteryl succinate in its free acid form, thereby resulting in a reduced bioavailability of cholesteryl succinate (as also observed in vivo as best shown in Tables 26 and 27).

An in vivo experiment was performed to determine the effect of alpha-TS on the energy status of rat tissues. Male Sprague-Dawley rats were administered alpha-TS (100 mg/kg, single ip dose) or olive oil (vehicle only, 0.2 ml, single ip dose). Three rats were used per treatment. The rats fasted for 24 hours after ip dosage prior to sacrifice and analysis of tissues. Table 16 shows the effect of the administering alpha-TS on the energy status of rat tissue.

TABLE 16

Effect of alpha-tocopherol succinate (+) or Vehicle (−) Administration on the Energy Status of Rat Tissue

| ATP (nmol/g) Alpha-TS | Glucose (μmol/g) Alpha-TS |
|---|---|

TABLE 16-continued

Effect of alpha-tocopherol succinate (+) or Vehicle
(−) Administration on the Energy Status of Rat Tissue

| Tissue | (−) | (+) | (−) | (+) |
|---|---|---|---|---|
| Liver | 428 ± 127 | 458 ± 57 | 23.2 ± 10.8 | 21.7 ± 9.7 |
| Kidney | 390 ± 95 | 515 ± 44+ | 4.1 ± 0.7 | 3.4 ± 1.1 |
| Heart | 2015 ± 483 | 2782 ± 868 | 8.7 ± 1.4 | 10.1 ± 1.7 |
| Lung | 247 ± 27 | 418 ± 18* | 4.2 ± 1.3 | 4.1 ± 0.5 |
| Brain | 112 ± 42 | 293 ± 86* | N.D. | N.D. |
| Blood | 224 ± 42 | 647 ± 29* | 6.0 ± 1.1 | 4.8 ± 0.3 |

| | Lactate (μmol/g) Alpha-TS | | Glycogen (μmol/g) Alpha-TS | |
|---|---|---|---|---|
| Tissue | (−) | (+) | (−) | (+) |
| Liver | 3.07 ± .58 | 3.36 ± .20 | 179 ± 26 | 778 ± 98* |
| Kidney | 4.77 ± .66 | 3.10 ± .21* | 122 ± 50 | 211 ± 44+ |
| Heart | 16.69 ± 1.56 | 10.84 ± 2.67* | 428 ± 49 | 4321 ± 946* |
| Lung | 2.06 ± .92 | 2.24 ± .29 | 168 ± 15 | 634 ± 133* |
| Brain | 11.61 ± .60 | 7.82 ± .20* | 1425 ± 224 | 1396 ± 372 |
| Blood | 1.05 ± .34 | 1.68 ± .06* | 25 ± 1 | 117 ± 26* |

Results are expressed as X ± SE (n = 3), with tissue from each rat analyzed in triplicate. Three rats per treatment.
*p < .05, as compared to vehicle control
+p < .1 as compared with vehicle control All of the organs tested were greatly affected by the administration of alpha-TS. Dramatic increases in ATP or glycogen levels were observed for all tissues and a dramatic decrease in tissue lactate levels were found in the kidney, heart and brain. Increases in tissue lactate levels have been suggested to promote tissue injury during toxic insults. The in vivo results may suggest that the potentiation of cellular energy status is responsible for the cytoprotective properties. The in vivo study confirms that all tissues and organ systems will benefit from ionizable tocopheryl administration.

In vivo experiments have been conducted with male Sprague-Dawley rats to determine particular tocopherol and succinate analogs which are cytoprotective. Several tocopherol and succinate analogs were tested for $CCl_4$ induced lethality. A single dose of the tocopherol or succinate analog was administered twenty four hours prior to orally administering 2.9 g $CCl_4$/kg body weight. Three to six animals were analyzed per treatment. The rats were monitored for seven days. Table 17 shows the days survived after treatment with $CCl_4$.

TABLE 17

Protective Effect of Tocopherol and Succinate Analogs
on Carbon Tetrachloride Induced Lethality in Rats

| Tocopherol or Succinate Analog Administered | Days Survived After $CCl_4$ Treatment |
|---|---|
| Vehicle Control (Olive Oil) | 2 |
| Alpha-Tocopherol (100 mg/kg) | 3 |
| Succinic Acid (100 mg/kg) | 2 |
| Succinic Acid, Na Salt (1 g/kg) | 2 |
| Monomethyl Succinate (1 g/kg) | 2 |
| Dimethyl Succinate (1 g/kg) | 2 |
| Alpha-Tocopheryl Succinate (50 or 100 mg/Kg) | >7* |
| Alpha-Tocopheryl Succinate (25 m/kg) | >7*[a] |
| Alpha-Tocopheryl Succinate, K+ Salt (100 mg/kg) | >7* |
| Alpha-Tocopheryl Succinate Methyl Ester (100 mg/kg) | >7*[a] |
| Alpha-Tocopheryl Succinate Polyethylene Glycol Ester (100 or 200 mg/Kg) | >7* |
| Alpha-Tocopheryl Succinate Polyethylene Glycol Ester (200 mg/Kg, iv) | >7* |
| Alpha-Tocopheryl Succinate Polyethylene Glycol Ester (200 mg/kg, oral) | 2[a] |
| Alpha-Tocopheryl 3-Methyl Succinate (100 mg/kg) | 2[a] |
| Alpha-Tocopheryl Glutarate (100 mg/kg) | 2 |

TABLE 17-continued

Protective Effect of Tocopherol and Succinate Analogs
on Carbon Tetrachloride Induced Lethality in Rats

| Tocopherol or Succinate Analog Administered | Days Survived After $CCl_4$ Treatment |
|---|---|
| dl, alpha-Tocopheryl Phosphate, Na Salt (100 mg/kg) | 3 |
| Cholesterol (100 mg/kg) | 2 |
| Cholesteryl Succinate (100 mg/kg) | >7* |

[a]two to three animals in group survived.
*P < .05, as compared to vehicle control Most of the analogs were administered intraperitoneally; however, PEG analogs dissolved in saline were administered intravenously or orally as well. Rats pretreated with cholesterol or the vehicle alone (olive oil) died within two days. In contrast, rats which received succinate esters of tocopherol and cholesterol were protected against the lethal effects of $CCl_4$. FIGS. 5a and 5b show the structure versus the activity for the analogs reported in table 17.

Table 18 shows the results of in vivo experiments where rats were orally given a 2.9 g $CCl_4$ g/kg body weight dose after fasting for twenty four hours. The survival of the rats in each category was monitored and an $LD_{50}$ value was calculated (greater than three rats in each category of treatment were used). Providing rats with a 100 mg/kg body weight i.p. dose of either alpha-TS or cholesteryl succinate twenty four hours prior to the $CCl_4$ dose protected the rats from death and the calculated $LD_{50}$ values for rats in both groups was 4.4 g $CCl_4$/kg. Table 18 also shows the SGOT levels (AST levels) for rats which were pretreated with some of the tocopherol and succinate analogs and were sacrificed 48 hours after receiving a 1.0 g/kg body weight oral dose of $CCl_4$. As discussed above, SGOT levels provide a clinical assessment of hepatotoxicity (liver damage). Contrasting the group of control rats which received vehicle alone (no $CCl_4$) with rats which received an i.p. dose of cholesteryl succinate, it can be seen that the cholesteryl succinate protected the rats from the hepatotoxic effects of $CCl_4$. This protection has been confirmed by histopathology.

Ionizable congeners of aromatic and aliphatic alcohols can be used for a variety of purposes which capitalize on their cytoprotective function such as the suppression and/or prevention of cancer, protection against the deficits induced by ischemic challenge (i.e., heart disease, stroke, and organ transplantation), protection against Alzheimer's and Parkinson's disease, protection against tissue-damaging effect of environmental pollutants, preservation of tissues, wound healing, suppression of the aging process, and protection against toxic therapeutic drugs. Normal tissue can be protected from damage induced by cancer therapeutic agents such as adriamycin, radiation, and the like, using ionizable congeners of aromatic and aliphatic alcohols. Ionizable congeners of aromatic and aliphatic alcohols also inhibit tumor cell growth and prevent the inducement of neoplasia in normal tissue. Ionizable congeners of aromatic and aliphatic alcohols can be used to preserve organs and blood that are stored for transplantation, facilitate the process of wound healing and lessen the likelihood of scarring, protect against premature aging of the skin induced by environmental factors such as the sun and wind, and protect body tissues against the "normal" process of degradation with age. Except for use in conjunction with wound healing and ischemic challenge, the ionizable congeners of aromatic and aliphatic alcohols are optimally administered prior to the toxic or degradative challenge (prophylactically).

Prasad and others have reported that alpha-TS administration (10μM) inhibits tumor cell growth (mouse melanoma cells B-16; mouse neuroblastoma cells NBP2; human neuroblastoma cells; and human prostate cells in culture). In addition, it has been reported that alpha-TS has the ability to induce morphological differentiation in mouse melanoma cells so that the resultant new cells resemble normal melanocytes (a reversion from carcinogenic to normal tissue). Shklar and others have reported a dramatic regression in chemically-induced tumors (epidermoid carcinomas) of the hamster cheek pouch by local administration of alpha-TS. In all of the reported studies, it has been assumed that the antitumor effect of alpha-TS stems from the release of alpha-T from alpha-TS.

Figure 6:
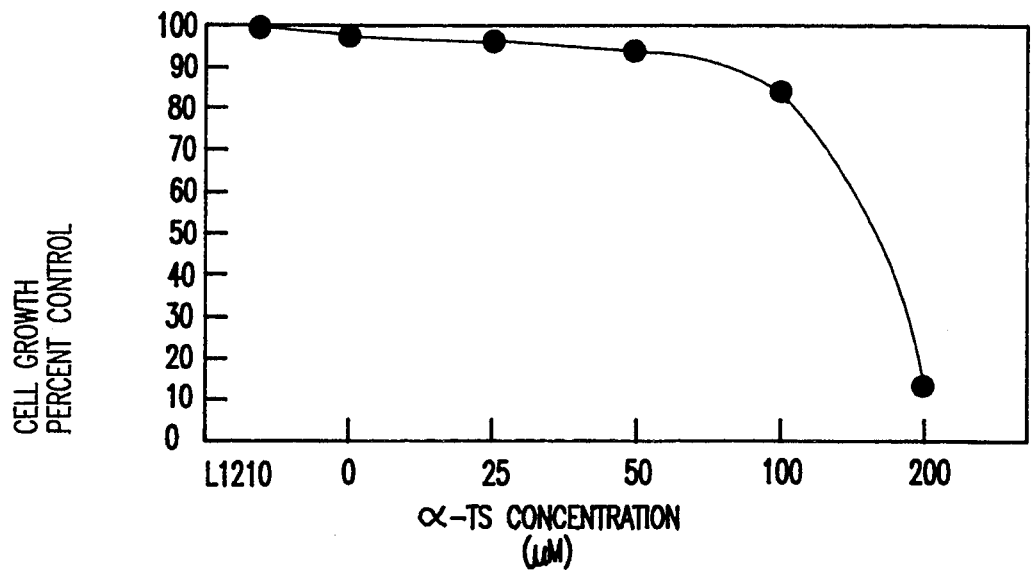
FIG. 6 is a graph showing the inhibition of L1210 murine leukemia cell growth in vitro with increasing concentrations of alpha-TS.
Figure 7:
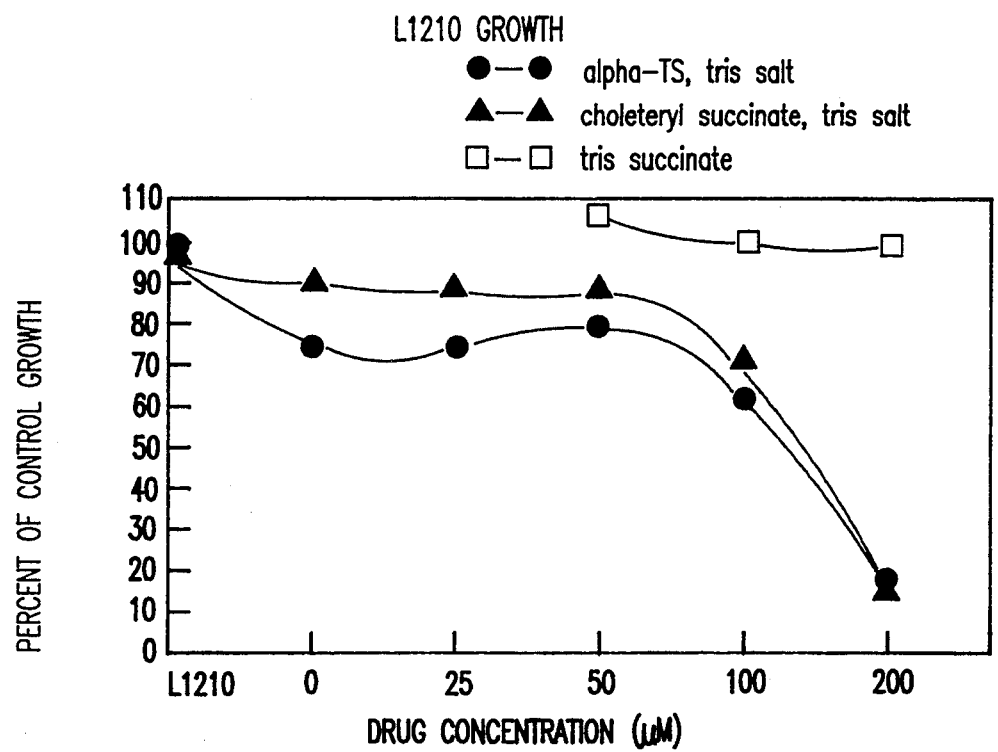
FIG. 7 is a graph showing the inhibition of L1210 murine leukemia cell growth cytotoxicity in vitro with increasing concentrations of alpha-TS tris salt and cholesteryl succinate tris salt and the lack of anticytotoxic activity of tris succinate, and the absence of an effect on tumor cell growth by tris succinate.
Figure 8A:
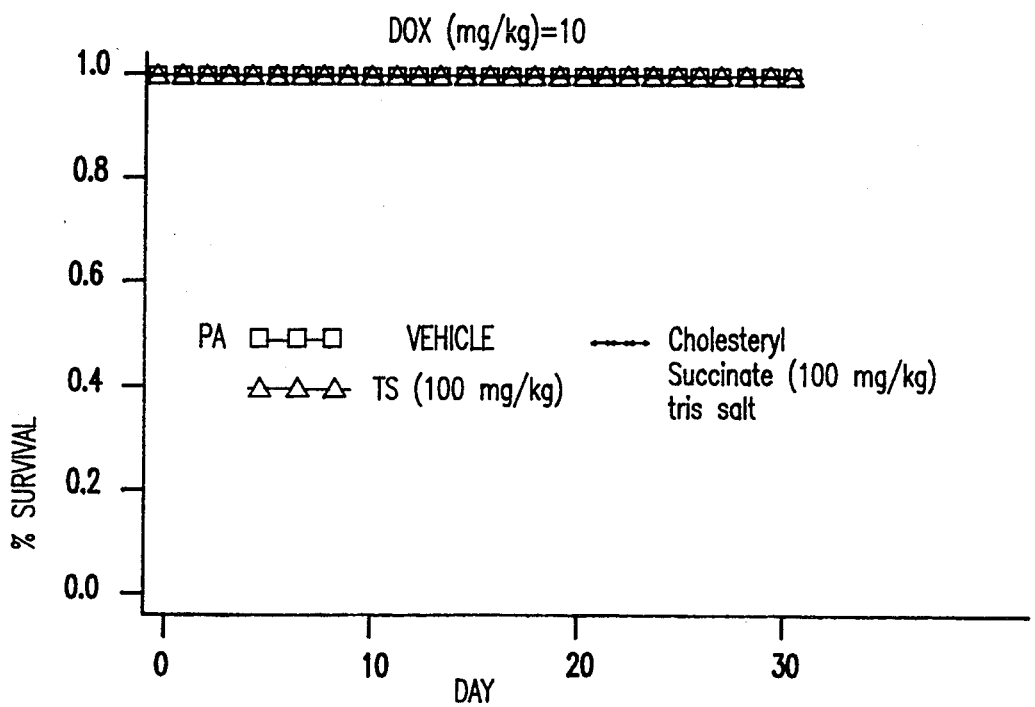
FIGS. 8a–8d are graphs shown the in vivo protective effects of cholesteryl succinate and alpha-TS against doxirubicon for normal tissue.
Figure 8B:
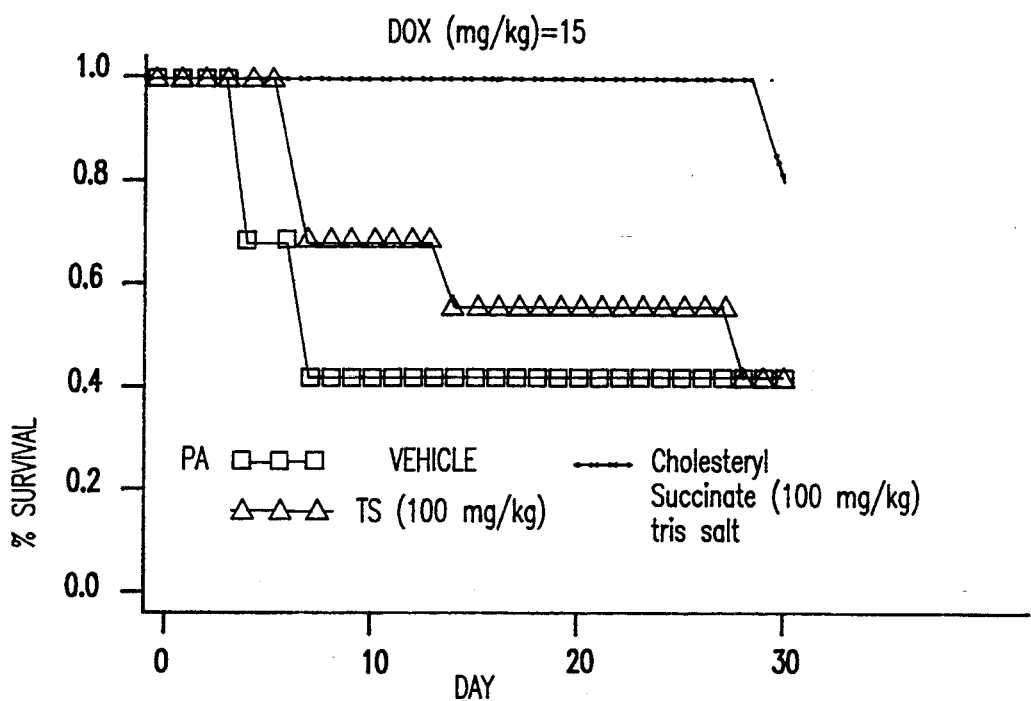
Figure 8C:
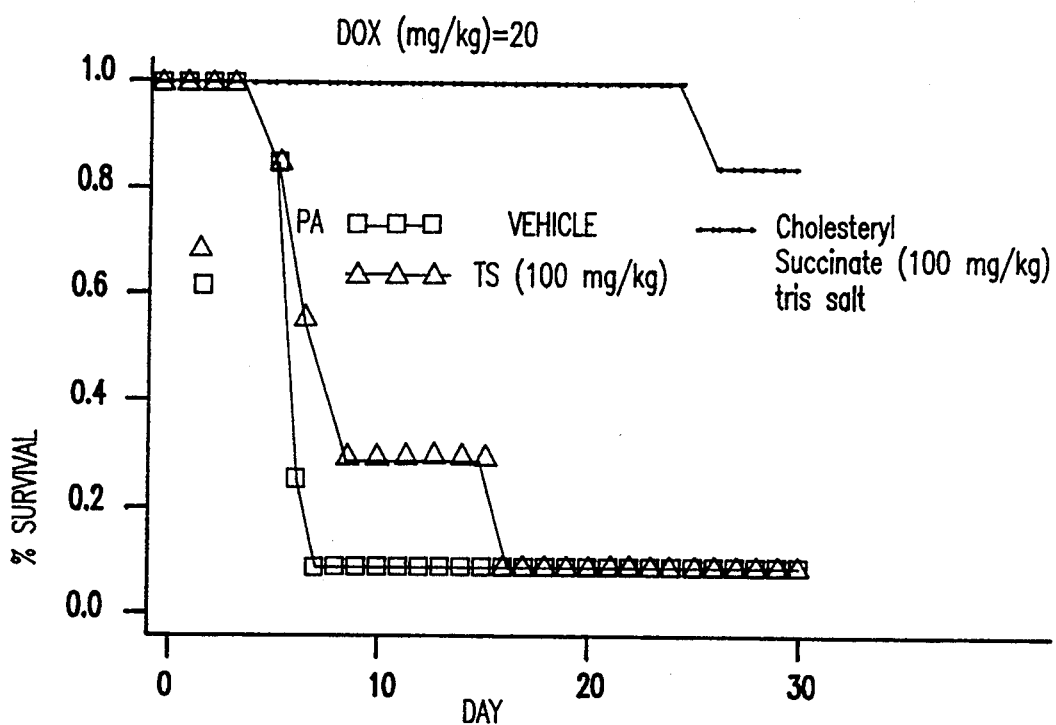
Figure 8D:
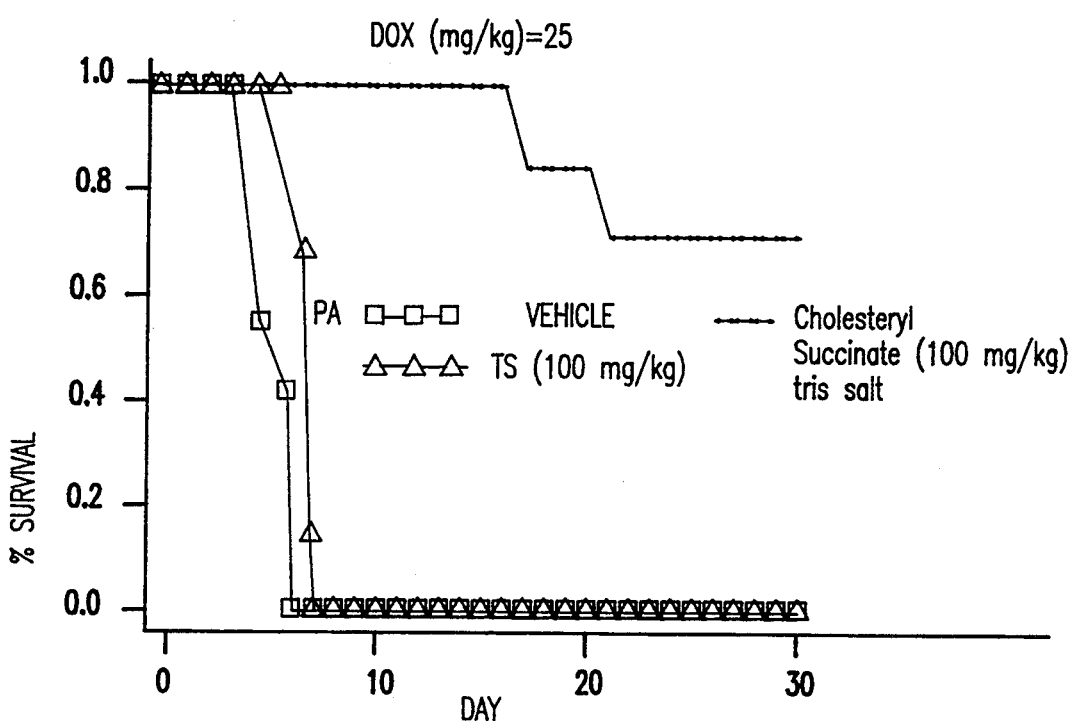

Experiments have been conducted in vitro and in vivo to examine the effect of alpha-TS on the growth of murine L1210 leukemia cells and these studies confirm the previous reports that alpha-TS administration inhibits tumor cell growth. These studies also show that cholesteryl succinate inhibits tumor cell growth and that the use of the tris salt of cholesteryl succinate and alpha-TS is advantageous over the free acid forms. FIG. 6 shows the dose response of alpha-TS on the growth of murine L1210 leukemia cells in suspension cultures where the L1210 cells were incubated in RPMI-1640 medium with 10% fetal bovine serum at a density of $0.5*10^5$ cells/ml and were treated with varying amounts of alpha-TS free acid or vehicle (ethyl alcohol) and were incubated for 72 hours followed by a cell number determination. It can be seen that alpha-TS (free acid) administration at concentration greater than 100 μM significantly suppresses the growth rate of L1210 cells. Similar in vitro experiments were conducted with cholesteryl succinate tris salt and alpha-TS tris salt. FIG. 7 shows that cholesteryl succinate tris salt and alpha-TS tris salt both significantly suppress the growth rate of L1210 cells, while tris succinate alone had no effect on the growth rate of these tumor cells. Table 19 shows that the administration of both alpha-TS tris salt and cholesteryl succinate tris salt (100 mg/kg body weight, i.p., single dose) in vivo results in a small, but significant, growth arrest of implanted murine L1210 leukemia cells in CDF1 mice as measured by enhanced survival time. In addition, the administration of alpha-TS tris salt and cholesteryl succinate tris salt did not damage normal tissue. Hence, the cytoprotective effect of alpha-TS is not related to the release of alpha-T, but do to the presence of the ionizable congener (cholesteryl succinate does not release alpha-T).

Dr. Borek and others have shown that alpha-TS protects a variety of cell types against the carcinogenic effects of radiation and cancer causing chemicals. These effects were attributed to the presence of tocopherol, despite the fact that other analogues of alpha-tocopherol, such as alpha-TA were ineffective in the same studies. Table 20 demonstrates that both alpha-TS and cholesteryl succinate protect in vivo tissues from the damage normally produced by the potent cancer-causing chemical $CCl_4$. Succinate analogs were administered to male Sprague-Dawley rats 20 hours prior to a 1 g $CCl_4$/kg body weight oral challenge and the AST and ALT serum enzyme levels were measured 48 hours after the challenge. Tris succinate did not provide protection against the $CCl_4$ challenge, nor did cholesteryl succinate tris salt when administered orally. Cholesteryl succinate tris salt and alpha-TS tris salt when administered by intraperitoneal injection provided protection against $CCl_4$ induced hepatotoxicity. The results also indicate that cholesteryl succinate is more cytoprotective than alpha-TS, a result which has not been previously shown. Hence, the ionizable congener of the aromatic and aliphatic alcohol is responsible for the cytoprotection, as opposed to the release of alpha-T.

Figure 9A:
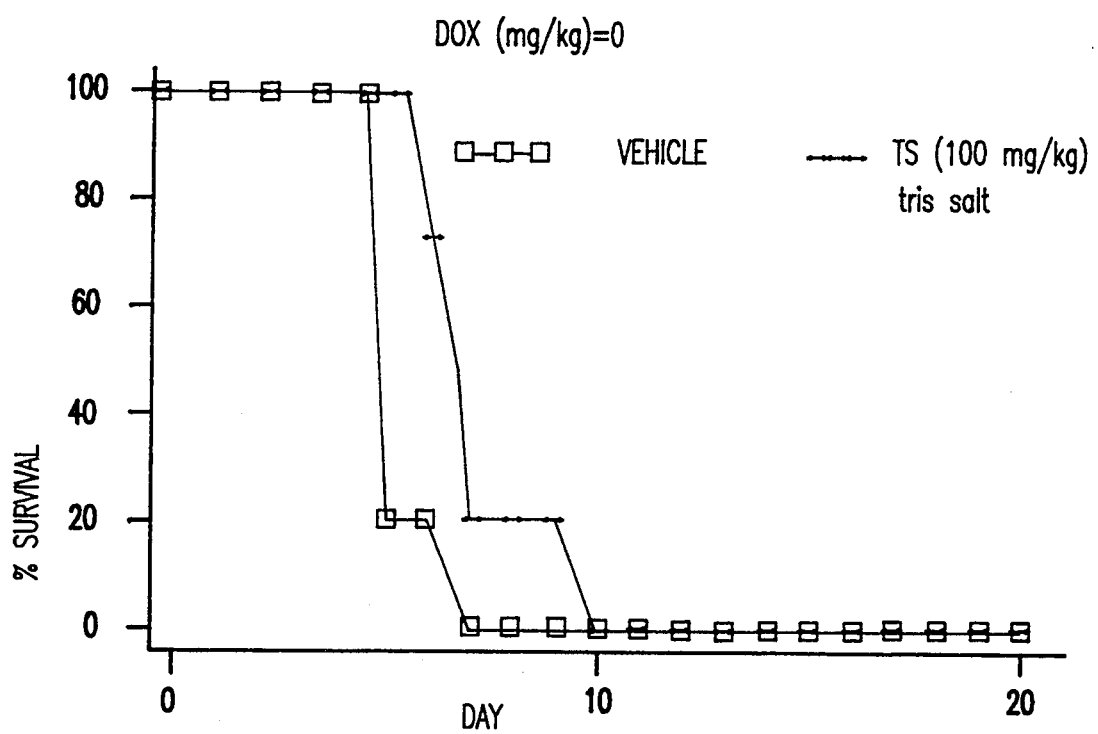
FIGS. 9a–9d are graphs showing the in vivo effects of alpha-TS tris salt against doxirubicon for neoplastic tissue.
Figure 9B:
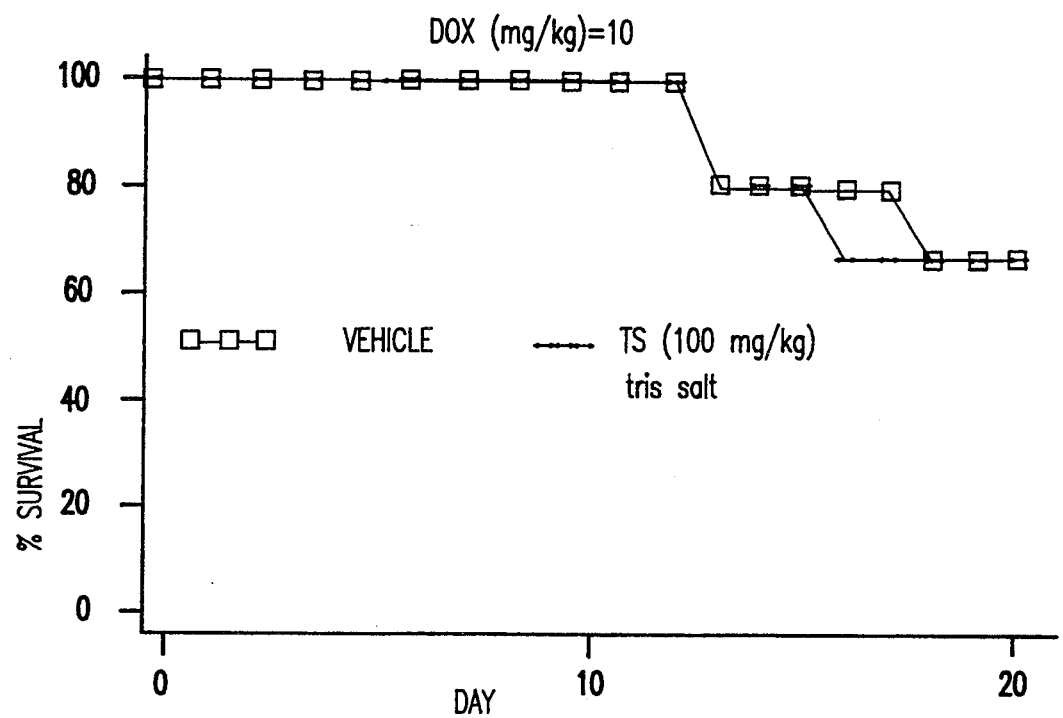
Figure 9C:
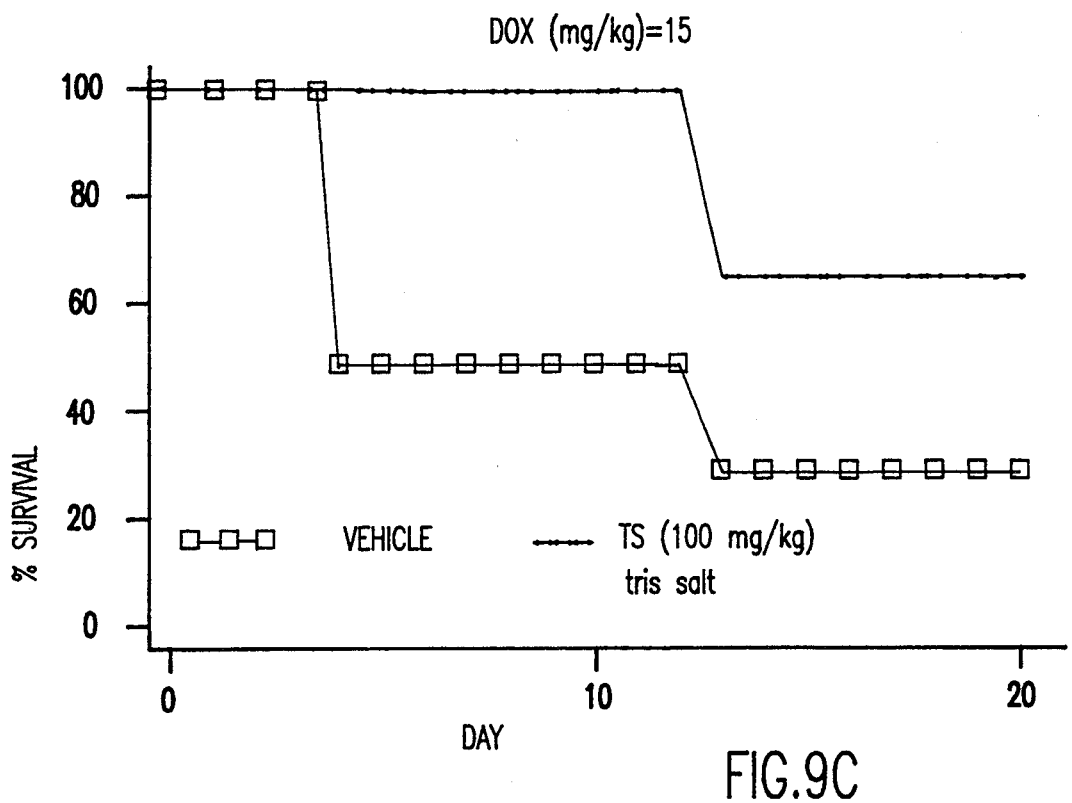
Figure 9D:
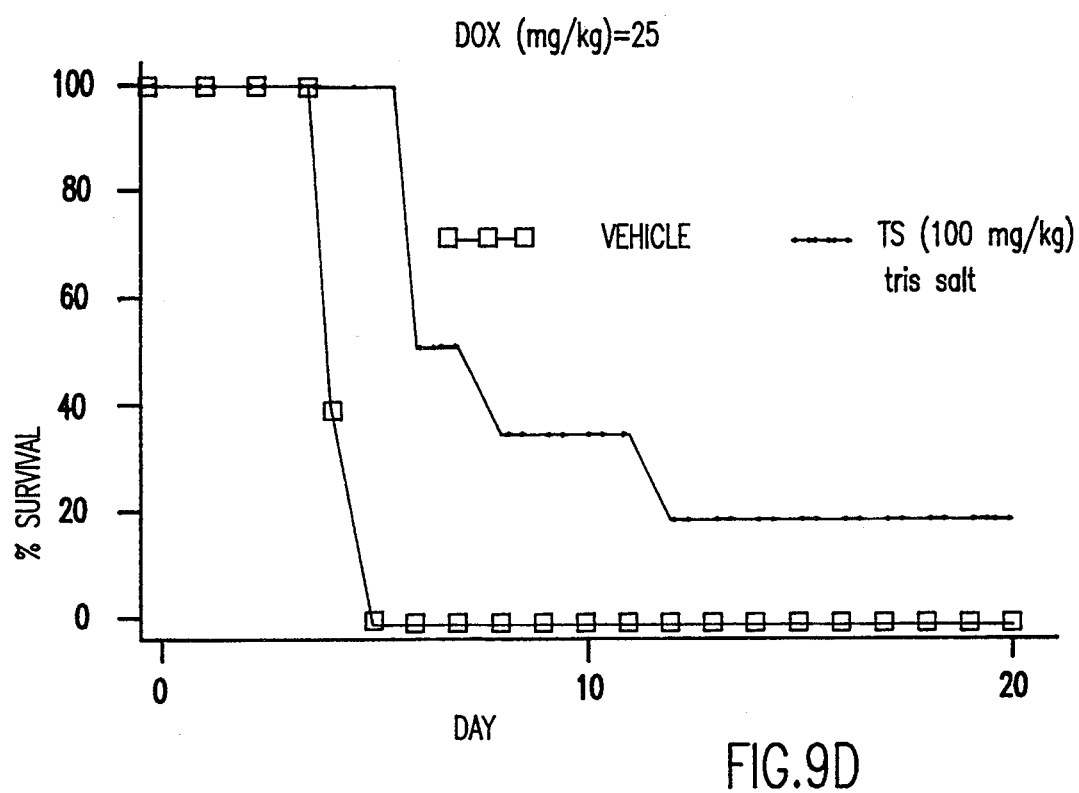
Figures 12A, 12B:
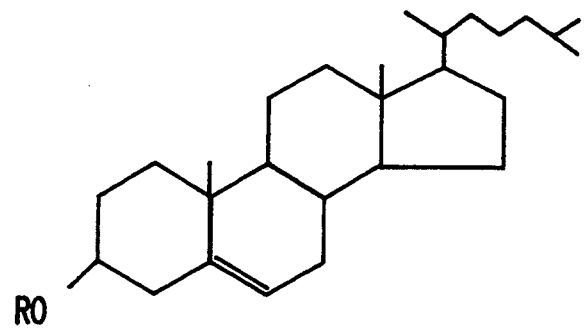
Figures 13A, 13B:
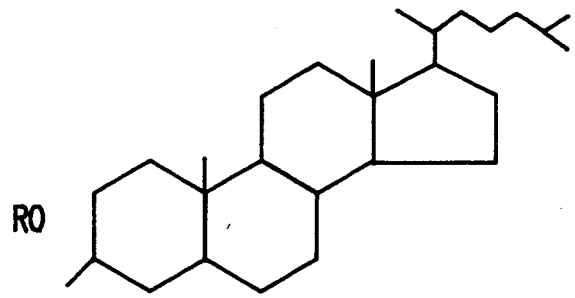
Figures 14A, 14B:
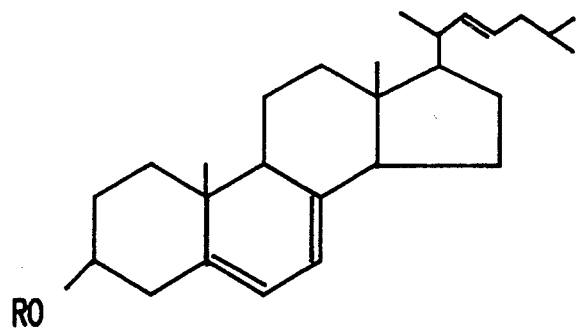

In vivo experiments have been conducted which show that both the alpha-TS and cholesteryl succinate tris salts protect normal tissues from doxorubicin (DOX, also called adriamycin which is an anti-tumor, anticarcinogenic agent). The experiments were conducted in accordance with NCI Protocol 1,100. FIGS. 8a–d show the experimental results obtained when male $CDF_1$ mice (n=6) received either vehicle only or 100mg/kg body weight i.p. dose of either alpha-TS or cholesteryl succinate 20 hours prior to DOX administration. FIGS. 8a–d respectively show the results obtained when the mice received 10, 15, 20, and 25 mg DOX/kg body weight. The treated mice survived significantly longer than untreated mice or mice treated only with vehicle. Hence, it can be seen that alpha-TS and cholesteryl succinate protect normal tissues against the lethal effects of DOX and that cholesteryl succinate is more effective than alpha-TS. Further in vivo experiments have demonstrated that the protective activity of alpha-TS against the anticarcinogenic agent DOX does not occur in neoplastic tissues. FIGS. 9a–d show the experimental results obtained when male $CDF_1$ mice (n=1) were injected (i.p.) with $10^6$ murine L1210 leukemia cells followed immediately by an injection of alpha-TS tris salt (100 mg/kg, i.p.) or saline injection (vehicle), and twenty hours later (Day=0) each mouse in three of the groups was i.p. injected with 15, 20, or 25 mg DOX/kg body weight (FIGS. 8a–d, respectively). Survival was monitored for twenty days. FIG. 9a shows that tumor cells in the absence of DOX will kill both treated and untreated animals; however, reference back to Table 19 does show that combined administration of alpha-TS with tumor cells slightly, but significantly, increases the animals survival time (promotes the destruction of tumor cells). FIG. 9b shows that when the mice are given 10 mg/kg of the antitumor agent DOX, the survival of the tumor bearing mice is dramatically increased, however, the administration of alpha-TS appears to have no effect on the survival of DOX treated animals (indicating that alpha-TS does not protect tumor cells from the lethal effects of DOX). FIGS. 12c–d show that mice dosed with higher concentrations of DOX, e.g., 15 and 25 mg DOX/kg body weight, were provided with significant protection from DOX by the administration of alpha-TS (which supports the data presented in FIGS. 8b–d with normal tissues).

In vivo experiments have been conducted which demonstrate that cholesteryl succinate protects against liver ischemia/reperfusion-induced lethality or injury. Table 21 shows the results of a total ischemia study where male Sprague-Dawley rats were subjected to global occlusion of the hepatic artery and portal vein for 60 minutes followed by reperfusion for 24 hours. 20 hours prior to global occlusion, one group of 10 rats was provided with 64 mg cholesterol/kg body weight and 100 mg tris succinate/kg body weight by i.p. injection, and another group of 10 rats was provided with 100 mg cholesteryl succinate/kg body weight. A control group of rats was only partially occluded for the one hour period. Ninety percent of the rats pretreated with cholesteryl succinate tris salt survived while only 10% of those pretreated with the combination of cholesterol and tris succinate survived. Table 22 of a partial ischemia study where male Sprague-Dawley rats were subjected to occlusion of the blood supply to the left lateral and median lobes of the liver for 60 minutes followed by reperfusion for 24 hours. During this time, the normal blood supply to the other lobes of the liver was maintained. This treatment does not result in lethality (liver failure), but does produce significant liver damage. Serum was obtained for AST and ALT measurements. One group of rats was provided with an i.p. dose of saline (same volume as used for other treatments) and the other group of rats was provided with an i.p. dose of 100 mg cholesteryl succinate tris salt/kg body weight 20 hours prior to inducing partial ischemia. Table 22 demonstrates that cholesteryl succinate tris salt administration prior to or during the ischemic challenge significantly reduces ischemia-induced liver damage. Protection was observed for both fed and fasted rats. In addition, experiments have also been conducted which demonstrate that rats which were administered cholesterol plus tris succinate were not protected from the hepatotoxic effects of partial ischemia. Additional experiments were conducted which show that significant ($p<0.05$) protection against partial ischemia-induced liver damage occurs when rats are pretreated with a 25 mg cholesteryl succinate tris salt/kg body weight i.p. dose (ALT $358\pm38$) as compared to vehicle alone (saline)(ALT $1027\pm235$) and with dihydrocholesterol sulfate, sodium salt (ALT $1305\pm568$) when compared to dihydrocholesterol plus sodium sulfate (ALT $3262\pm1850$).

The data from these in vivo experiments demonstrate that ionizable congeners of aromatic and aliphatic alcohols, and particularly cholesteryl succinate and dihydrocholesterol sulfate, can be used to protect against ischemia induced injury. In addition, these compounds have been shown to be therapeutic whether used prophylactically or administered at the time of injury. Thus, these compounds can be used to protect against injuries caused by heart attacks, stroke, and injuries consequent with the blood supply to an area being compromised. It is expected that the ionizable congeners of aromatic and aliphatic alcohols will also have significant value in transplantation surgery.

Figure 10:
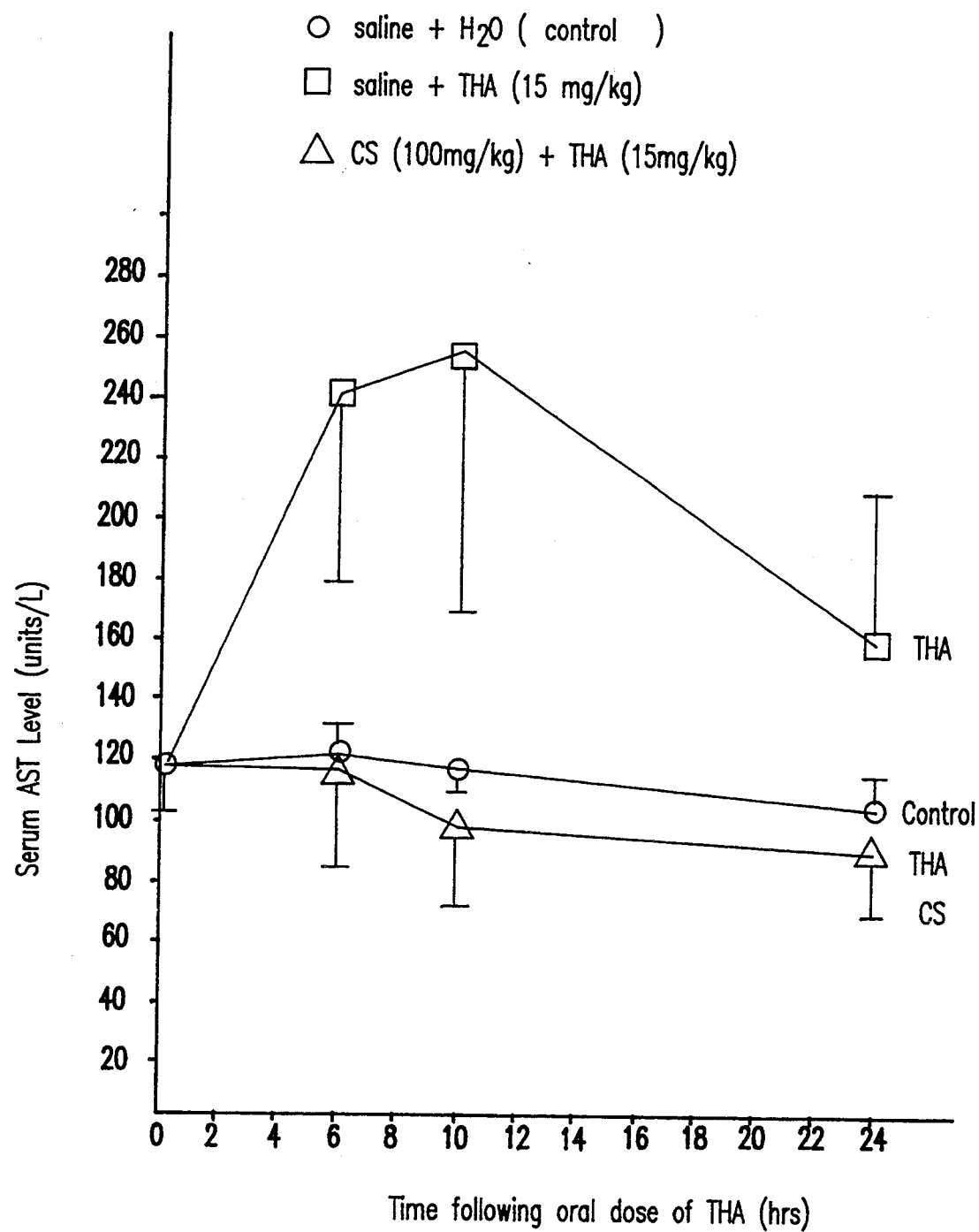
FIGS. 10 and 11 are graphs showing the in vivo protective effects of cholesteryl succinate against tetrahydroamino acridine (THS)-induced hepatotoxicity.
Figure 11:
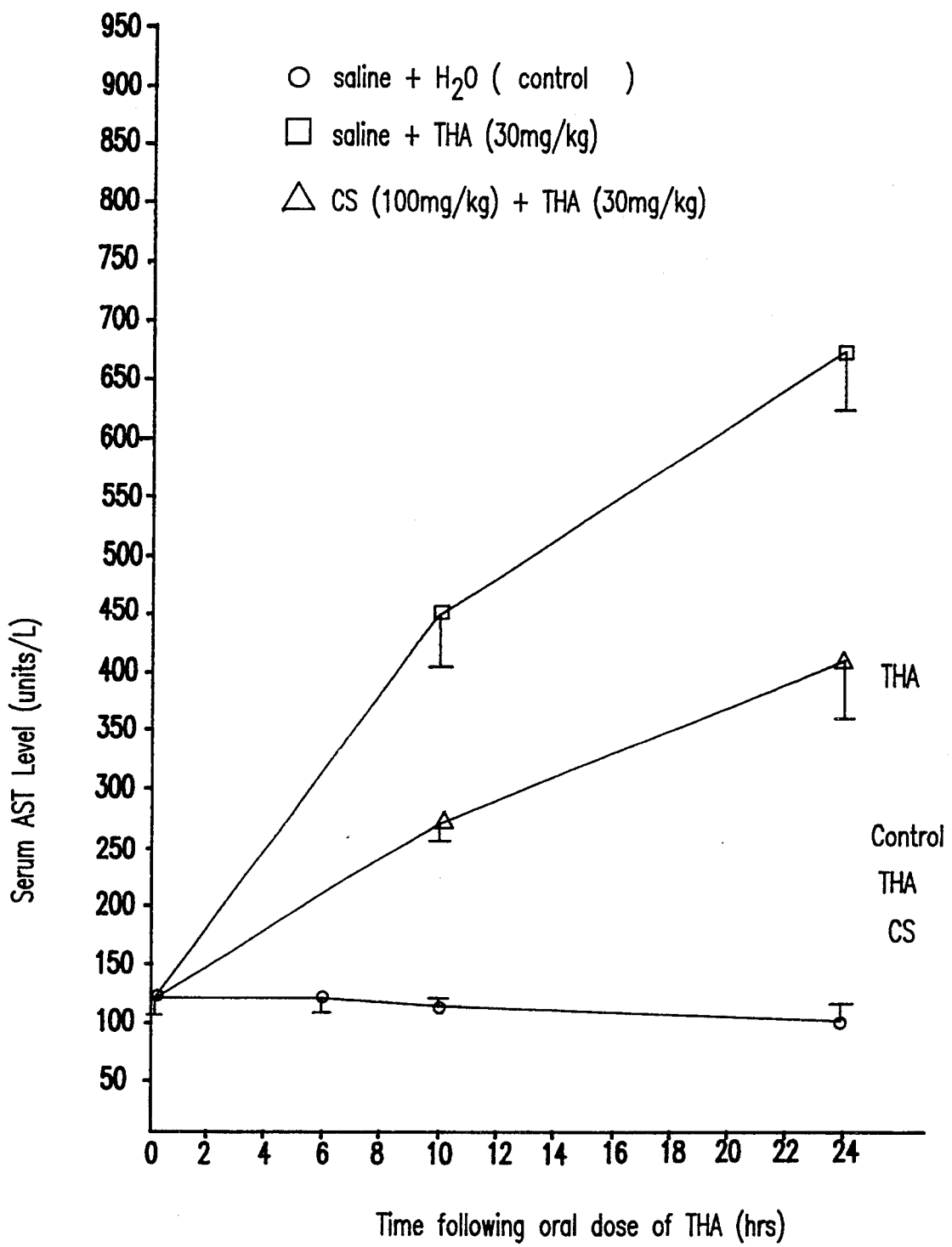
Figures 15A, 15B:
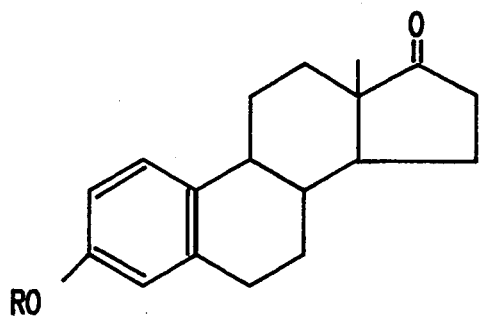
Figures 16A, 16B:
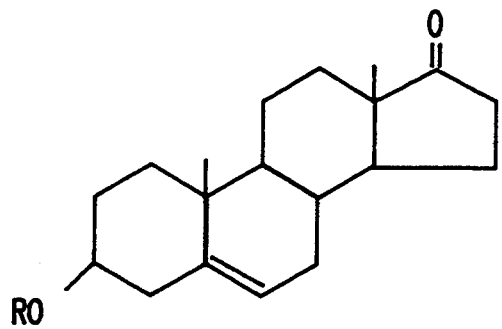

In vivo experiments have been conducted which demonstrate that cholesteryl succinate protects against the hepatotoxic effects of therapeutic drugs such as acetaminophen (AP) and tetrahydroaminoacridine (THA). FIG. 15 shows the effects on AST and ALT serum levels for male Sprague-Dawley rats which are given a 2 g/kg body weight oral dose of acetaminophen. Providing the rats with a 100 mg/kg body weight i.p. dose of cholesteryl succinate tris salt 20 hrs prior to administration of the acetaminophen challenge resulted in significant protection against the hepatotoxic effects of this drug as compared to control rats given an equal dose of tris succinate. FIGS. 10 and 11 show the results of in vivo experiments where male Sprague-Dawley rats were given an oral dose of 15 or 30 mg THA/kg body weight, respectively. In the experiments, one group of rats was provided with an i.p. dose of 100 mg cholesteryl succinate tris salt/kg body weight 20 hours prior to the THA challenge, another group of rats only received the THA challenge, and the last group of rats acted as a control and were not challenged. The serum AST levels were determined with respect to time after the THA challenge. In both FIGS. 10 and 11, it is demonstrated that prior treatment with cholesteryl succinate protects against the hepatotoxicity resulting from THA. Table 24 also shows that prior treatment with cholesteryl succinate resulted in an increase in the secretions generally associated with the effects of THA on acetylcholine release in the central nervous system. These secretory effects normally accompany the beneficial influences of THA on Alzheimer's disease; hence, cholesteryl succinate may facilitate the anti-Alzheimer's effects of THA as well as protect against THA-mediated hepatotoxicity.

The toxicity elicited by numerous therapeutic agents results from the metabolism of these compounds in the liver. In vivo experiments have been conducted with alpha-TS and cholesteryl succinate to determine their effect on metabolism via the pentobarbitone-induced sleeping time test. The duration of pentobarbitone-induced sleeping time is directly dependent on the metabolism of pentobarbitone in the liver. Table 25 shows that alpha-TS and cholesteryl succinate administered before the pentobarbitone-induced sleep may slightly increase sleeping time, but not significantly. In contrast, a drug known to interfere with drug metabolism in the liver (metyrapone 100 mg/kg body weight, i.p.) significantly increased (8 fold, $p<0.001$) the pentobarbitone induced sleeping time. These results indicate that alpha-TS and cholesteryl succinate induced protection do not result from their effect on drug metabolism.

Structure, dose, time of pretreatment, and route of administration of cholesteryl succinate can all have an effect on $CCl_4$-induced hepatotoxicity. Table 26 shows that both the tris salt and the free acid of cholesteryl succinate are cytoprotective agents; however, only cholesteryl succinate tris salt is significantly cytoprotective in vivo when compared to the vehicle control. The tris salt forms a fine micellular suspension that appears to have high bioavailability when injected intraperitoneally. In contrast, the free acid is insoluble in an aqueous medium and is, therefore, less available for uptake. This same effect was also demonstrated for alpha-TS. As shown in Table 27, the tris salt of alpha-TS is more protective than the free acid.

Table 28 shows cholesteryl succinate tris salt is protective over a wide range of dosages. There are significant ($p<0,001$) cytoprotective effects produced when 50, 100 and 200 mg cholesteryl succinate/kg body weight when administered by i.p. injection 20 hrs prior to an oral 1 g $CCl_4$/kg body weight challenge. Optimal doses are 100 mg/kg or greater. Table 29 shows cholesteryl succinate tris salt is protective when given 20 hrs prior to $CCl_4$ administration, but not effective when given at intervals 30 minutes or shorter prior to $CCl_4$ administration or after $CCl_4$ administration. The long pretreatment times to achieve cytoprotection may indicate that cholesteryl succinate operates by inducing endogenous cellular processes. As shown in Table 20, cytoprotection was coincident with i.p. injections of cholesteryl succinate, but was not induced when administered by oral garage.

Table 30 shows the effect of in vivo administration of a wide variety of ionizable congeners of aromatic and aliphatic alcohols on $CCl_4$-induced hepatotoxicity. Similar to the experiments were described above, the ionizable congeners were administered to Sprague-Dawley rats by i.p. injection of a 100 mg ionizable congener/kg body weight dose 20 hours prior to oral administration of a 1 g/kg dose of CCl$_4$, and the AST and ALT levels were measured 48 hours after the CCl$_4$ challenge. Hepatoprotection was based on a comparison with the AST and ALT levels found in rats treated only with the vehicle control. Table 30 shows that alpha-TS tris salt, cholesteryl succinate tris salt, cholesteryl 3-sulfate sodium salt, cholesteryl hydrogen phthalate, dihydrocholesterol sulfate sodium salt, dihydrocholesterol succinate free acid and tris salt, and linoleyl succinate were all effective in protecting against hepatotoxicity. Table 30 also shows that some ionizable congeners were not effective. Table 31 discuss the results reported in Table 30 in further detail and provide additional experimental data.

Table 31 shows that the administration of cholesterol succinate tris salt 20 hours prior to the administration of 1 g/kg (oral garage) of CCl$_4$, results in complete protection for Sprague-Dawley rats as measured by serum enzyme levels. In contrast, the administration of cholesterol and cholesterol acetate provided no protection. Table 32 shows that pretreatment with cholesterol plus succinic acid also provides no protection from a CCl$_4$ challenge. In addition, Table 32 shows that cholesteryl succinate tris salt and alpha-TS, when administered by i.p. dosage using PEG 400 as the vehicle, provide effective hepatotoxic properties, and that cholesteryl succinate tris salt is more effective than alpha-TS. Tables 33 and 34 show that cholesteryl 3-sulfate sodium salt and cholesteryl hydrogen phthalate proved to be potent cytoprotective agents in vivo. Tables 35–37 show that the administration of dihydrocholesteryl succinate free acid or tris salt or dihydrocholesteryl sulfate sodium salt (100 mg/kg i.p.) 20 hours prior to the oral administration of a 1 g CCl$_4$/kg body weight to male Sprague-Dawley rats resulted in complete protection against hepatotoxicity as measured by serum enzyme levels. In contrast, the administration of the sterol (dihydrocholesterol) plus sodium sulfate produced no significant cytoprotection. Hence, the results suggest that neither the succinate nor the cholesterol molecule is essential for cytoprotection; rather, it is the ionizable lipophilic molecule that is primarily responsible for cytoprotection.

Table 38 shows that the administration of either ergosterol succinate tris salt or ergosterol sulfate potassium salt (100 mg/kg i.p.) 20 hours prior to the administration of an oral (1 mg/kg) dose of CCl$_4$ to Male Sprague-Dawley rats resulted in protection against hepatotoxicity as measured by serum enzyme levels. Table 39 shows that the administration of ergosterol alone also results in cytoprotection from toxic CCl$_4$ insults. Table 39 also shows that dehydroepiandrosterone (DHEA) derivatives do not provide protection against hepatotoxicity, but that linoleyl succinate (free acid) does provide some cytoprotection. With reference back to Table 35, it can be seen that pretreatment of the Sprague-Dawley rats with linoleyl alcohol does not provide cytoprotection and, in fact, it potentiates CCl$_4$ toxicity. This is evidence of the anticytotoxic effect of ionizable congeners, wherein a toxic drug, such as linoleyl alcohol, is made non-toxic or cytoprotective by the addition of an ionizable congener. Table 41 shows that retinoic acid and retinol acetate also potentiated CCl$_4$ toxicity. Tables 33, 35, 37 and 40 show that the straight chain aliphatic alcohols and their derivatives, such as lauryl sulfate sodium salt, palmityl alcohol, palmityl succinate, phytol, and phytol succinate were generally not protective. Comparing Tables 34, 40, and 42 it can be seen that pretreatment of Sprague Dawley rats with estrone 3-succinate (free acid) or estrone sulfate potassium salt resulted in slight cytoprotection that was not greater than that observed for non-ionizable derivatives estrone and estrone acetate administration. Comparing the data for the estrone analogs with the DHEA data suggest that optimal cytoprotection may be induced with an ionizable congener of a sterol molecule. With reference back to Table 33, no cytoprotection was observed using hydrocortisone 21-succinate. Hence, it is suggested that the ionizable congener may need to be attached at position 3 of the sterol molecule for anticytotoxic activity. FIGS. 12a–b to 22a–b show the relationship between the chemical structure, the presence of an ionizable congener, and the cytoprotection provided by the compounds discussed above in conjunction with Tables 30–42.

The experimental results demonstrate that cytoprotection results from accumulating an intact ionizable congener of an aromatic or aliphatic alcohol in the cell. Cellular accumulation of alpha-TS, an ionizable congener of an aromatic alcohol, is continuous and gradual (1.65 nmol/10$^6$ cells/hr; 25 $\mu$M dose) with a slow cellular release of succinate (0.65 nmol/10$^6$ cells/hr., as measured by alpha-tocopherol release; 25 $\mu$M dose). Release of the succinate moiety occurs through the action of cellular esterases and the succinate molecule acts as a substrate for increased energy production. Ionizable congeners of aromatic and aliphatic alcohols include the succinic ester of tocopherol, the methyl ester of tocopheryl succinic acid, the PEG ester of tocopheryl succinic acid, the succinic acid ester of cholesterol, dihydrocholesteryl succinate or sulfate, cholesterol succinate or phthalate, ergosterol succinate or sulfate, linoleyl succinate or any other ionizable ester or ether derivative of aromatic and aliphatic alcohols and their pharmaceutically acceptable salts and tris salts. By altering the ionizable side chain of the aromatic or aliphatic alcohol, anticytotoxic compounds will be created. The distance between the ionizable group and the aromatic carbon ring or the aliphatic ring or chain may be varied by increasing or decreasing the carbon chain length. For example, instead of tocopheryl succinate (4 carbons) or cholesteryl succinate (4 carbons), esters of other dicarboxylic acids can be made; such as oxalic acid (2 carbons), malonic acid (3 carbons), adipic acid (6 carbons), and phtalic acid, et cetera. The number of carbon double bond carbons in the side chain between the ionizable group and the aromatic or aliphatic alcohol group can be varied. For example, aromatic and aliphatic esters of fumaric acid and maleic acid can be synthesized. The ionic strength of the ionizable side chain on the aromatic or aliphatic alcohol can be varied. For example, the number of ionizable groups on the side chain (citrate, hydroxy succinate; etc.) can be increased or the number of ionizable groups (diester of alpha-TP) can be reduced. The chemical nature of the ionizable side chain can be varied by synthesizing tocopherol esters, tocopheryl phosphate esters, tocopheryl glutarate esters, tocopheryl succinate esters, or other aromatic or aliphatic esters of cellular constituents such as amino acids (lysine, arginine, cysteine, aspartate, glutamate), proteins (glutathione) lipids (phosphatidylcholine, omega-3 fatty acids), nucleic acids (adenosine, AMP), carbohydrates (glucuronic acid, glucose, fructose), and taurine (thiol ester). The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be cytoprotective such as retinyl phosphate (vitamin A analog), dithiotheitol, ascorbic acid (vitamin C) and reduced ubiquinone, metal chelators (EDTA), omega-3 fatty acids, calcium antagonists, and antagonists of excitatory amino acids (adenosine derivatives of alpha-amino adipate). The chemical nature of the ionizable side chain can be varied by synthesizing tocopherol congeners or other aromatic or aliphatic congeners with an ether linkage between the side chain and the aromatic carbon ring of tocopherol or a sterol or with bulky side chains or aromatic groups situated in close proximity to the ester linkage (e.g., 2,2 dimethyl succinate). Diesters of alpha-T can be formulated with succinate (e.g., alpha-T-Succinate-T-alpha). These chemical alterations will retard or prevent the hydrolysis of the bond between the aromatic ring of tocopherol and the ionizable side chain. The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be involved in essential cellular processes such as substrates for cellular energy production (e.g., gluceraldehyde 3-phosphate, 3-phosphoglyceryl phosphate, phosphoenol pyruvate, phosphocreatine, malate, oxalacetate and alpha-ketoglutarate, and glutarate). By altering the lipophilic aromatic or aliphatic alcohol, anticytotoxic, procytotoxic and therapeutic compounds can be produced. Phenolic or aromatic compounds can be used for the attachment of an ionizable side chain. Such phenolic compounds might include tocopherol, trolox (chromamol ring of tocopherol), butylated hydroxytoluene (BHT), butylated hydroxylanisole (BHA), tannins (polyphenols, e.g., ellagic acid or corilagin), phytol, bactoprenol, co-enzyme Q, butoxyphenol, anthracycline antibiotics, and heterocyclic alcohols (pyridines, pyramidines, purines, etc.). Aliphatic compounds containing hydroxyl groups can be used for the attachment of an ionizable side chain. Such aliphatic compounds might include cholesterol, glycol polymers (propylene glycol or polyoxyethylene glycol), glycerin related compounds (glycerin, glycerol phosphate, monoacylglycerol, diacylglycerol, phosphatidylglycerol, cardiolipin, phosphatidylinostiol, or sphingosine), steroids and their derivatives (estradiol, estriol, testosterone, methandriol (anabolic steroid), methylprednisolone, prednisolone, vitamins and their derivatives (retinal, riboflavin, pyridoxal), prostaglandins and their derivatives (PGE$_2$, PGI2, iloprost, PGBx, or long chain fatty acids), or heterocyclic alcohols (pyroles, furans, imadozoles). The chemical nature of the ionizable side chain can be varied by synthesizing tocopherol esters, tocopheryl phosphate esters, tocopheryl glutarate esters, tocopheryl succinate esters, or other aromatic or aliphatic esters of compounds known to be cytotoxic (including the inhibition of cellular energy production, e.g., malonate, 3-phosphoglyceryl arsenate or halogenated derivatives of tricarboxylic acid cycle substrates, e.g., succinate)(See Gershon et al, J. Med. Chem. 20:606 (1979)). The chemical nature of the ionizable side chain can be varied by synthesizing tocopherol esters, tocopheryl phosphate esters, tocopheryl glutarate esters, tocopheryl succinate esters, or other aromatic and aliphatic esters of therapeutic drugs. This formulation should promote the cellular uptake and cellular retention of drugs thus providing a cellular reservoir for the release of drugs at critical cellular sites. For example, the cellular uptake of genetically engineered peptides and other products could be facilitated by their chemical attachment to aromatic and aliphatic alcohols. For another example, a recently discovered antibacterial agent that specifically inhibits lipopolysaccharide synthesis, is limited by its inability to penetrate the bacterial membrane (See, Goldman et al., Nature, 329, 162 (1987) and Goldman et al, Science News, 132:180 (1987)). Peptides have been chemically attached to this antibacterial agent to promote bacterial uptake; however, these carriers are short lived in vivo and do not provide penetration into all bacterium. Combining alpha-T with the antibacterial agent [alpha-C(1,5-anhydro-7-amino-2,7-dideoxy-D-mannoheptopyranosyl)-carboxylate] through an ester linkage will produce an ionizable congener that will promote tocopheryl congener bacterium uptake and retention of the therapeutic agent (antibacterial) with its cellular release from tocopherol resulting from the action of bacterial esterases.

TABLE 18

Protective Effect of Tocopherol and Succinate Analogs on Carbon Tetrachloride Induced Lethality and Hepatotoxicity in Rats

| Tocopherol or Succinate Analog Administered[a] | Survival after CCl$_4$ treatment[b] | Calculated LD$_{50}$ (g CCl$_4$/kg) | SGOT[c] Levels (10$^3$ units/L) |
|---|---|---|---|
| Vehicle (No CCl$_4$) | Yes | | 0.12 ± .03 |
| Vehicle (olive oil) | No | 2.6 | 3.57 ± 1.18 |
| Alpha-Tocopherol | No | 1.5 | |
| Succinic Acid | No | 2.6 | |
| Alpha-Tocopheryl Succinate | Yes | 4.4 | |
| Cholesteryl Succinate tris salt | Yes | 4.4 | 0.10 ± 0.03 |
| Cholesterol | No | 2.6 | 4.08 ± 2.45 |
| Alpha-Tocopheryl Glutarate | No | 2.6 | |
| Alpha-Tocopheryl 3-Methyl Succinate | No | 2.6 | |

[a]100 mg/kg given i.p., 24 hours prior to CCl$_4$ insult, n > 3.
[b]2.9 g/kg CCl$_4$ given orally after fasting for 24 hours.
LD$_{50}$ - Oral dose of CCl$_4$ required for 50% lethality
[c]SGOT levels were measured 48 hours following a 1.0 g/kg oral dose of CCl$_4$.

TABLE 19

EFFECT OF ALPHA-TOCOPHERYL SUCCINATE AND CHOLESTERYL SUCCINATE ADMINISTRATION ON SURVIVAL OF CDF$_1$ MICE FOLLOWING INJECTION OF 10$^6$ L1210 LEUKEMIA CELLS

| Tocopherol or Succinate Analog Administered[a] | Survival Time (days) |
|---|---|
| Vehicle Control (Saline) | 6.0 ± 0.0 |
| Tocopheryl Succinate, tris salt | 7.6 ± 0.6** |
| Cholesteryl Succinate, tris salt | 6.8 ± 0.4* |

[a]100 mg/kg given i.p., immediately following tumor cell injection.
[b]Survival time was identical for succinate and vehicle treated groups.
*$p < 0.01$ as compared to succinate group, ± SD, n = 5.
**$p < 0.001$ as compared to succinate group, ± SD, n = 5.

TABLE 20

EFFECT OF IN VIVO ADMINISTRATION OF IONIZABLE CONGENERS OF AROMATIC AND ALIPHATIC ALCOHOLS ON CCl$_4$ - INDUCED HEPATOTOXICITY

| Analog Administered[a] | Serum Enzyme Levels[b] | |
|---|---|---|
| | AST (10$^3$ units/L) | ALT (10$^3$ units/L) |
| Tris Succinate (100 mg/kg, ip) (No CCl$_4$) | 0.11 ± 0.02 | 0.048 ± 0.005 |

TABLE 20-continued

EFFECT OF IN VIVO ADMINISTRATION OF IONIZABLE CONGENERS OF AROMATIC AND ALIPHATIC ALCOHOLS ON CCl$_4$ - INDUCED HEPATOTOXICITY

| Analog Administered[a] | Serum Enzyme Levels[b] | |
|---|---|---|
| | AST ($10^3$ units/L) | ALT ($10^3$ units/L) |
| Tris Succinate (100 mg/kg, ip) | 11.22 ± 3.15 | 3.617 ± 0.858 |
| Cholesteryl Succinate Tris Salt (100 mg/kg, ip) | 0.41 ± 0.08** | 0.122 ± 0.034** |
| Cholesteryl Succinate Tris Salt (100 mg/kg, oral) | 12.51 ± 41.31 | 4.09 ± 1.191 |
| Alpha Tocopheryl Succinate Tris Salt (100 mg/kg, ip) | 1.86 ± 1.11* | 0.371 ± 0.246** |

[a]Given 20 hours prior to CCl$_4$ administration.
[b]Measured 48 hours following 1 g/kg oral dose of CCl$_4$
*$p < 0.01$ as compared to Tris Succinate (with CCl$_4$) treatment, ∓ ± SD, n = 3–5. All animals were fasted 20 hours prior to CCl$_4$ administration.
**$p < 0.001$, ± SD, n = 4–5.

TABLE 21

EFFECT OF CHOLESTERYL SUCCINATE ADMINISTRATION ON LIVER ISCHEMIA/REPERFUSION-INDUCED LETHALITY

| Ischemia | Pretreatment[a] | % Survival |
|---|---|---|
| Global | Cholesterol (64 mg/kg, ip) + Tris Succinate (100 mg/kg, ip) | 10% (1/10) |
| Global | Cholesteryl Succinate Tris Salt (100 mg/kg, ip) | 90% (9/10) |
| Partial | None | 100% (3/3) |

[a]Global (total) or partial liver ischemia was induced 20 hours following pretreatment with the compounds listed above. After 60 minutes of ischemia, reperfusion was initiated and continued for 24 hrs.

TABLE 22

EFFECT OF CHOLESTERYL SUCCINATE ADMINISTRATION ON PARTIAL LIVER ISCHEMIA/REPERFUSION-INDUCED INJURY[a]

| Time of Treatment | Treatment | Serum Enzyme Levels (Units/L) | |
|---|---|---|---|
| | | AST | ALT |
| 20 hours prior to ischemia | Saline (100 mg/kg, ip) | 6450 ± 2903 | 2907 ± 1094 |
| 20 hours prior to ischemia | Cholesteryl succinate tris salt (100 mg/kg, ip) | 1800 ± 904* | 554 ± 213*** |
| During ischemia | Saline (100 mg/kg, ip) | 1960 ± 389 | 933 ± 238 |
| During ischemia | Cholesteryl succinate tris salt (100 mg/kg, ip) | 967 ± 68** | 387 ± 155* |

[a]Partial liver ischemia was induced in male Sprague Dawley rats (fed) for 60 min, followed by reperfusion for 24 hours, at which time serum was obtained for AST and ALT measurements. Sham operations (Without ischemia) resulted in AST and ALT values of 261 ± 37 and 58 ± 6 respectively.
*$p < 0.05$ as compared to saline vehicle control group, ± SD, n = 3–4.
**$p < 0.02$ as compared to saline vehicle control group, ± SD, n = 3–4.
***$p < 0.01$ as compared to saline vehicle control group, ± SD, n = 3–4.

TABLE 23

EFFECT OF CHOLESTERYL SUCCINATE ADMINISTRATION OF ACETAMINOPHEN (AP) - INDUCED HEPATOTOXICITY

| Analog Administered | Serum AST Level[a] (Units/L) | Serum ALT Level[a] (Units/L) |
|---|---|---|
| Tris Succinate (100 mg/kg, ip) (No AP) | 93 ± 34 | 50 ± 7 |
| Tris Succinate (100 mg/kg, ip) (20 hrs prior to AP) | 2286 ± 1190 | 623 ± 339 |
| Cholesteryl Succinate (100 mg/kg, ip) Tris Salt (20 hrs prior to AP) | 785 ± 495* | 158 ± 77** |

[a]Measured 48 hours following a 2 g/kg oral dose of Acetaminophen.
*$p < 0.05$ as compared to Tris Succinate (20 hours prior) treatment, ± SD, n = 4–6. All rats were fed during the entire experiment.
**$p < 0.02$.

TABLE 24

EFFECT OF CHOLESTERYL SUCCINATE TRIS SALT (CS) ADMINISTRATION ON TETRAHYDROAMINO-ACRIDINE (THA) - INDUCED SIDE EFFECTS IN MALE SPRAGUE-DAWLEY RATS

| THA (mg/kg) | Change From Control | | | | | |
|---|---|---|---|---|---|---|
| | Tremors* | | Salivation* | | Survival* | |
| | Veh. | CS. | Veh. | CS. | Veh. | CS. |
| 30.0 | 3.0 ± 0.0 | 4.0 ± 0.0[a] | 2.2 ± 0.4 | 4.0 ± 0.0[a] | 100% | 40%[a] |

Control = vehicle (ip) + distilled water (oral dose), CS - cholesterol succinate tris salt (100 mg/kg, ip), Veh. - saline, ip. Tremor and salivation were rated on a 0 to 4 scale with 0 meaning no effect. CS and vehicle were given 20 hours prior to THA administration.
[a]$p < 0.001$ as compared to vehicle ±SD, n = 5.
*Measured 3–5 hrs. following oral dose of THA to fasted (20 hrs) rats.

TABLE 25

EFFECTS OF TOCOPHERYL SUCCINATE AND CHOLESTERYL SUCCINATE ADMINISTRATION ON PENTOBARBITONE (PB) SLEEPING TIME IN THE RAT

| Pretreatment[a] | Sleeping Time (min)[b] | Nutritional Status Prior to PB |
|---|---|---|
| Vehicle (olive oil) | 72 ± 14 | Fasted 24 hours |
| Alpha Tocopheryl Succinate (100 mg/kg, ip) | 86 ± 1 | |
| Cholesterol (64 mg/kg, ip) + Tris Succinate (59 mg/kg, ip) | 117 ± 30 | Fasted 24 hours |
| Cholesteryl Succinate Tris Salt (100 mg/kg, ip) | 148 ± 40 | |
| Cholesterol (64 mg/kg, ip) + Tris Succinate (59 mg/kg, ip) | 89 ± 1 | Fed |
| Cholesteryl Succinate Tris Salt (100 mg/kg, ip) | 102 ± 16 | |
| Vehicle (corn oil) | 120 ± 9 | Fasted 24 hours |
| Metyrapone (100 mg/kg, ip) | 900 ± 120* | |

[a]Rats are pretreated, with the compounds listed, 20 hours prior to PB except metyrapone which was given 30 min prior to PB.
[b]Pentobarbitone administration (50 mg/kg, ip).
*$p < 0.001$ as compared to control, ±SEM, n = 3–5.

TABLE 26

EFFECT OF CHOLESTERYL SUCCINATE CHEMICAL FORM (FREE ACID OR TRIS SALT) ON ITS PROTECTIVE CAPACITY AGAINST CCl$_4$ HEPATOTOXICITY IN VIVO

| Analog Administered[a] | Serum AST Levels ($10^3$ units/L)[b] | |
|---|---|---|
| | 24 hrs | 48 hrs |
| Vehicle Control (olive oil) (with CCl$_4$) | 2.33 ± 0.35 | 4.39 ± .33 |
| Cholesteryl Succinate free acid (100 mg/kg, ip) | 1.84 ± 1.13 | 1.90 ± 2.64 |
| Cholesteryl Succinate, tris salt (100 mg/kg, ip) | 0.57 ± 0.38* | 0.19 ± 0.07* |

[a]Given 20 hours prior to CCl$_4$ administration.
[b]Measured at the time intervals indicated following a 2 g/kg oral dose of CCl$_4$.
*$p < 0.001$ as compared to Vehicle Control (with CCl$_4$), $\bar{x}$ ± SD, n = 3–5.

TABLE 27

EFFECT OF TOCOPHERYL SUCCINATE CHEMICAL FORM (FREE ACID OR TRIS SALT) ON ITS PROTECTIVE CAPACITY AGAINST CCl$_4$ HEPATOTOXICITY IN VIVO

| Analog Administered[a] | Serum AST Levels ($10^3$ units/L)[b] | |
|---|---|---|
| | AST ($10^3$ units/L) | ALT ($10^3$ units/L) |
| Vehicle Control (olive oil) (with CCl$_4$) | 4.41 ± 2.05 | 1.95 ± 0.71 |
| Alpha Tocopheryl Succinate free acid (100 mg/kg, ip) | 2.06 ± 0.53 | 1.08 ± 0.23 |
| Alpha Tocopheryl Succinate tris salt (100 mg/kg, ip) | 0.79 ± 0.26* | 0.52 ± 0.16* |

[a]Given 20 hours prior to CCl$_4$ administration.
[b]Measured 48 hours following a 1 g/kg oral dose of CCl$_4$.
*$p < 0.01$ as compared to Vehicle Control and Tocopherol Succinate Free Acid treatments, $\bar{x}$ ± SD, n = 3–4.

TABLE 28

EFFECT OF THE DOSE OF CHOLESTERYL SUCCINATE TRIS SALT ON ITS PROTECTIVE CAPACITY AGAINST CCl$_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (saline) | 7.58 ± 2.10 | 3.16 ± 0.48 |
| Cholesteryl Succinate tris salt (200 mg/kg, ip) | 0.16 ± 0.08* | 0.03 ± 0.01* |
| Cholesteryl Succinate tris salt (100 mg/kg, ip) | 0.22 ± 0.06* | 0.04 ± 0.02* |
| Cholesteryl Succinate tris salt (50 mg/kg, ip) | 0.56 ± 0.35* | 0.16 ± 0.11* |

[a]Given 20 hours prior to CCl$_4$ administration.
[b]Measured 48 hours following 1 g/kg oral dose of CCl$_4$.
*$p < 0.001$ as compared to Vehicle Control (with CCl$_4$), ±SD, n = 3–5.

TABLE 29

EFFECT OF PRETREATMENT TIME ON CHOLESTERYL SUCCINATE TRIS SALT-MEDIATED PROTECTION AGAINST CCl$_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (saline) | 6.72 ± 2.76 | 2.60 ± 1.52 |
| Cholesteryl Succinate tris salt (100 mg/kg, ip) (20 hours prior to CCl$_4$) | 0.12 ± 0.02* | 0.04 ± 0.01* |
| Cholesteryl Succinate tris salt (100 mg/kg, ip) (30 min prior to CCl$_4$) | 9.09 ± 4.38 | 2.12 ± 1.43 |
| Cholesteryl Succinate tris salt (100 mg/kg, ip) (immediately prior to CCl$_4$) | 6.69 ± 1.87 | 1.12 ± 1.38 |
| Cholesteryl Succinate tris salt (100 mg/kg, ip) (30 min after to CCl$_4$) | 7.87 ± 4.09 | 1.50 ± 0.79 |

[a]Measured 48 hours following 1 g/kg oral dose of CCl$_4$.
*$p < 0.001$ as compared to Vehicle control (with CCl$_4$), ±SD, n = 4–5.

TABLE 30

EFFECT OF IN VIVO ADMINISTRATION OF IONIZABLE CONGENERS OF AROMATIC AND ALIPHATIC ALCOHOLS ON CCl$_4$-INDUCED HEPATOTOXICITY

| Ionizable Congener Administered[a] | % Hepatoprotection[b] | Protective Potency[c] |
|---|---|---|
| Vehicle Control (without CCl$_4$) | 100% | |
| Vehicle Control (with CCl$_4$) | 0% | |
| Tocopherol Derivatives | | |
| Alpha tocopheryl succinate tris salt | 80% | ++ |
| Sterol Derivatives | | |
| Cholesteryl succinate tris salt | 100% | ++++ |
| Cholesteryl 3-sulfate, sodium salt | 90% | +++ |
| Cholesteryl hydrogen phthalate | 100% | ++++ |
| Dihydrocholesterol sulfate, sodium salt | 100% | +++ |
| Dihydrocholesterol succinate, tris salt | 100% | ++++ |
| Ergosterol sulfate, potassium salt | 86% | +++ |
| Ergosterol succinate, tris salt | 80% | +++ |
| Dehydroepiandrosterone 3-succinate | 0% | 0 |
| Dehydroepiandrosterone 3-sulfate | 4% | 0 |
| Hydrocortisone 21-succinate | 25% | 0 |
| Straight Chain Alcohol Derivatives | | |
| Lauryl sulfate, sodium salt | 26% | 0 |
| Palmityl succinate | 22% | 0 |
| Linoleyl succinate | 46% | + |
| Phytol succinate | 27% | 0 |
| Others | | |
| Retinoic acid (50 mg/kg, ip) | (−83%) | 0 |

[a]Given at a concentration of 100 mg/kg, ip., 20 hours prior to CCl$_4$ administration (except as noted).
[b]Measured 48 hours following a 1 g/kg oral dose of CCl$_4$. AST and ALT levels from experimental compounds were compared to vehicle controls to assess the % hepatoprotection.
[c]Protective potency was determined on a scale from 0 to 4, based on AST and ALT levels as compared to vehicle controls.

TABLE 31

EFFECT OF THE DOSE OF CHOLESTERYL SUCCINATE TRIS SALT ON ITS PROTECTIVE CAPACITY AGAINST CCl$_4$ HEPATOTOXICITY IN VIVO

| Analog Administered[a] | Serum Enzyme Levels[b] | |
|---|---|---|
| | AST ($10^3$ units/L) | ALT ($10^3$ units/L) |
| Vehicle Control (olive oil) (no CCl$_4$) | 0.12 ± 0.03 | 0.04 ± 0.01 |
| Vehicle Control (olive oil) (+CCl$_4$) | 3.57 ± 1.18 | 0.92 ± 0.14 |
| Cholesteryl Succinate tris salt (100 mg/kg, ip) | 0.10 ± 0.03* | 0.02 ± 0* |
| Cholesterol (100 mg/kg, ip) | 3.03 ± 0.84 | 1.16 ± 0.41 |
| Cholesterol acetate (100 mg/kg, ip) | 3.06 ± 1.06 | 0.96 ± 0.32 |

[a]Given 20 hours prior to CCl$_4$ administration.
[b]Measured 48 hours following 1 g/kg oral dose of CCl$_4$.
*$p < 0.001$ as compared to Vehicle Control (with CCl$_4$). ±SD, n = 3–5.

TABLE 32

EFFECT OF THE DOSE OF CHOLESTERYL SUCCINATE TRIS SALT ON ITS PROTECTIVE CAPACITY AGAINST $CCl_4$ HEPATOTOXICITY IN VIVO

| Analog Administered[a] | Serum AST Levels ($10^3$ units/L)[b] | | |
|---|---|---|---|
|  | 24 hrs | 48 hrs | 72 hrs |
| Vehicle Control (polyethylene glycol 400) (no $CCl_4$) | .12 ± .02 | .11 ± .03 | .13 ± .02 |
| Vehicle Control (with $CCl_4$) | .99 ± .36 | 1.04 ± .10 | .26 ± .11 |
| Cholesteryl Succinate tris salt (100 mg/kg, ip) | .19 ± .10*** | .10 ± .02**** | .10 ± .02** |
| Alpha Tocopheryl Succinate (100 mg/kg, ip) | .38 ± .15* | .39 ± .22*** | .14 ± .06 |
| Cholesterol (100 mg/kg, ip) + Succinic acid (50 mg/kg, ip) | .86 ± .16 | 1.66 ± .50 | .30 ± .07 |

[a]Given 20 hours prior to $CCl_4$ administration.
[b]Measured at the time intervals indicated following a 2 g/kg oral dose of $CCl_4$.
*$p < 0.05$ as compared to Vehicle Control (with $CCl_4$), ±SD, n = 3–5.
**$p < 0.02$ as compared to Vehicle Control (with $CCl_4$), ±SD, n = 3–5.
***$p < 0.01$ as compared to Vehicle Control (with $CCl_4$), ±SD, n = 3–5.
****$p < 0.001$ as compared to Vehicle Control (with $CCl_4$), ±SD, n = 3–5.

TABLE 33

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
|  | AST ($10^3$ units/L) | ALT ($10^3$ units/L) |
| Tris Succinate (100 mg/kg, ip) (No $CCl_4$) | 0.15 ± 5.02 | 0.058 ± .001 |
| Tris Succinate (100 mg/kg, ip) | 8.32 ± 2.65 | 2.135 ± .881 |
| Cholesteryl 3-Sulfate Sodium Salt (100 mg/kg, ip) | 0.86 ± 0.35** | 0.240 ± .133* |
| Palmityl Succinate Tris Salt (100 mg/kg, ip) | 6.54 ± 3.61 | 1.679 ± 0.881 |
| Palmityl Alcohol (100 mg/kg, ip) | 8.70 ± 3.00 | 1.840 ± 1.106 |
| Hydrocortisone 21-Succinate (100 mg/kg, ip) | 6.18 ± 3.15 | 1.596 ± 0.887 |

[a]Given 20 hours prior to $CCl_4$ administration.
[b]Measured 48 hours following 1 g/kg oral dose of $CCl_4$.
*$p < 0.01$ as compared to Control (with $CCl_4$), ±SD, n = 5.
**$p < 0.001$.

TABLE 34

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
|  | AST ($10^3$ units/L) | ALT ($10^3$ units/L) |
| Vehicle Control Polyethylene glycol 400, 4 ml/kg, ip) | 14.35 ± 2.98 | 4.08 ± 1.70 |
| Cholesteryl Succinate tris salt (100 mg/kg, ip) | 0.29 ± 0.22** | 0.07 ± 0.03** |
| Estrone sulfate, potassium salt (100 mg/kg, ip) | 4.19 ± 2.75* | 0.87 ± 0.59* |
| Dehydroepiandosterane 3-sulfate, sodium salt (100 mg/kg, ip) | 13.85 ± 0.37 | 3.89 ± 0.81 |
| Cholesterol hydrogen phthalate (100 mg/kg, ip) | 0.30 ± 0.12** | 0.06 ± 0.03** |
| Dihydrocholesterol sulfate, sodium salt (100 mg/kg, ip) | 0.15 ± 0.07** | 0.03 ± 0.03** |

[a]Given 20 hours prior to $CCl_4$ administration.
[b]Measured 48 hours following 1 g/kg oral dose of $CCl_4$.
*$p < 0.01$ as compared to Vehicle control (with $CCl_4$), ± SD, n = 3–5.
**$p < 0.001$ as compared to Vehicle control (with $CCl_4$), ± SD, n = 3–5.

TABLE 35

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
|  | AST ($10^3$ units/L) | ALT ($10^3$ units/L) |
| Vehicle Control (olive oil) | 8.35 ± 2.65 | 2.62 ± 0.70 |
| Cholesteryl Succinate tris salt (100 mg/kg, ip) | 0.22 ± 0.06*** | 0.04 ± 0.02*** |
| Dihydrocholesterol (80 mg/kg, ip) + Sodium sulfate (30 mg/kg, ip) | 6.63 ± 2.58 | 1.97 ± 0.59 |
| Dihydrocholesterol sulfate, sodium salt (100 mg/kg, ip) | 0.17 ± 0.04*** | 0.02 ± 0.01*** |
| Linoleyl succinate (100 mg/kg, ip) | 4.47 ± 2.21 | 1.44 ± 0.59* |
| Linoleyl alcohol (100 mg/kg, ip) | 15.60 ± 2.98** | 5.45 ± 1.10** |

[a]Given 20 hours prior to $CCl_4$ administration.
[b]Measured 48 hours following 1 g/kg oral dose of $CCl_4$.
*$p < 0.05$ as compared to Vehicle control (with $CCl_4$), ± SD, n = 3–5.
**$p < 0.01$ as compared to Vehicle control (with $CCl_4$), ± SD, n = 3–5.
***$p < 0.001$ as compared to Vehicle control (with $CCl_4$), ± SD, n = 3–5.

TABLE 36

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
|  | AST ($10^3$ units/L) | ALT ($10^3$ units/L) |
| Vehicle Control (olive oil) | 4.74 ± .70 | 3.56 ± 0.41 |
| Dihydrocholesterol succinate | 0.44 ± 0.29* | 0.39 ± 0.40* |

[a]Given 20 hours prior to $CCl_4$ administration.
[b]Measured 48 hours following 1 g/kg oral dose of $CCl_4$.
*$p < 0.001$ as compared to Vehicle control (with $CCl_4$), ± SD, n = 3–4.

TABLE 37

EFFECT OF IN VIVO ADMINISTRATION OF IONIZABLE CONGENERS OF AROMATIC AND ALIPHATIC ALCOHOLS ON $CCl_4$ - INDUCED HEPATOTOXICITY

| Analog Administered[a] | Serum Enzyme Levels[b] | |
|---|---|---|
|  | AST ($10^3$ units/L) | ALT ($10^3$ units/L) |
| Vehicle Control (olive oil) | 4.52 ± 1.48 | 2.61 ± 0.59 |
| Cholesteryl succinate, tris salt (100 mg/kg, ip) | 0.21 ± 0.03* | 0.09 ± 0.01* |
| Dihydrocholesteryl succinate, tris salt (100 mg/kg, ip) | 0.19 ± 0.05* | 0.09 ± 0.03* |

TABLE 37-continued
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Phytol succinate (100 mg/kg, ip) | 3.29 ± 0.51 | 1.70 ± 0.18 |
| Phytol (100 mg/kg, ip) | 4.71 ± 1.00 | 2.82 ± 0.54 |

[a]Given 20 hours prior to $CCl_4$ administration.
[b]Measured 48 hours following 1 g/kg oral dose of $CCl_4$.
*$p < 0.001$ as compared to vehicle control, ± SD, n = 3–5.

TABLE 38
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Vehicle Control (olive oil) (with $CCl_4$) | 3.99 ± 1.69 | 1.72 ± 0.76 |
| Ergosterol (100 mg/kg, ip) | 1.73 ± 0.58* | 0.93 ± 0.48* |
| Ergosterol sulfate, potassium salt (100 mg/kg, ip) | 0.58 ± 0.53** | 0.28 ± 0.37** |
| Ergosterol succinate, tris salt (100 mg/kg, ip) | 0.80 ± 0.28** | 0.46 ± 0.25** |

[a]Given 20 hours prior to $CCl_4$ administration.
[b]Measured 48 hours following 1 g/kg oral dose of $CCl_4$.
*$p < 0.05$ as compared to vehicle control (with $CCl_4$), $\bar{x}$ ± SD n = 3–5.
**$p < 0.01$ as compared to vehicle control (with $CCl_4$), $\bar{x}$ ± SD n = 3–5.

TABLE 39
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Vehicle Control (peanut oil) | 8.80 ± 1.51 | 3.05 ± 0.88 |
| Dehydroepiandosterone 3-succinate (100 mg/kg, ip) | 10.42 ± 3.36 | 3.89 ± 1.77 |
| Linoleyl succinate (100 mg/kg, ip) | 5.60 ± 1.30* | 1.95 ± 0.84 |
| Ergosterol (100 mg/kg, ip) | 1.90 ± 0.73** | 0.63 ± 0.45** |

[a]Given 20 hours prior to $CCl_4$ administration.
[b]Measured 48 hours following 1 g/kg oral dose of $CCl_4$.
*$p < 0.05$ as compared to Vehicle control (with $CCl_4$), ± SD, n = 3–5.
**$p < 0.01$ as compared to Vehicle control (with $CCl_4$), ± SD, n = 3–5.

TABLE 40
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Vehicle Control (saline) | 6.72 ± 2.76 | 2.60 ± 1.52 |
| Cholesteryl Succinate tris salt (100 mg/kg, ip) | 0.12 ± 0.02** | 0.04 ± 0.01** |
| Estrone 3-Succinate (100 mg/kg, ip) | 1.71 ± 1.00* | 0.51 ± 0.56* |
| Lauryl sulfate sodium salt (100 mg/kg, ip) | 5.00 ± 1.54 | 1.40 ± 0.59 |

[a]Given 20 hours prior to $CCl_4$ administration.
[b]Measured 48 hours following 1 g/kg oral dose of $CCl_4$.
*$p < 0.01$ as compared to Vehicle control (with $CCl_4$), ± SD, n = 3–5.
**$p < 0.001$ as compared to Vehicle control (with $CCl_4$), ± SD, n = 3–5.

TABLE 41
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Vehicle Control (olive oil) | 9.82 ± 1.46 | 2.33 ± 0.93 |
| Retinoic acid (50 mg/kg, ip) | 17.94 ± 0.71** | 6.14 ± 0.74** |
| Retinol acetate (50 mg/kg, ip) | 13.00 ± 2.11* | 5.17 ± 1.32* |

[a]Given 20 hours prior to $CCl_4$ administration.
[b]Measured 48 hours following 1 g/kg oral dose of $CCl_4$.
*$p < 0.05$ as compared to Vehicle control (with $CCl_4$), ± SD, n = 3–5.
**$p < 0.01$ as compared to Vehicle control (with $CCl_4$), ± SD, n = 3–5.

TABLE 42
EFFECT OF IN VIVO ADMINISTRATION
OF IONIZABLE CONGENERS OF AROMATIC
AND ALIPHATIC ALCOHOLS ON $CCl_4$ -
INDUCED HEPATOTOXICITY

| Analog Administered[a] | Serum Enzyme Levels[b] | |
|---|---|---|
| | AST ($10^3$ units/L) | ALT ($10^3$ units/L) |
| Vehicle Control (olive oil) | 3.03 ± 0.63 | 1.71 ± 0.29 |
| Estrone (100 mg/kg, ip) | 0.56 ± 0.45 | 0.33 ± 0.30 |
| Estrone Acetate (100 mg/kg, ip) | 0.53 ± 0.24 | 0.18 ± 0.08 |
| Estrone Succinate (100 mg/kg, ip) | 0.70 ± 0.20 | 0.32 ± 0.12 |

[a]Given 20 hours prior to $CCl_4$ administration.
[b]Measured 48 hours following 1 g/kg oral dose of $CCl_4$.

While the invention has been described in terms of the preferred embodiment of the invention, those skilled in the art will recognize that other cytoprotective agents and different concentrations can be employed within the spirit and scope of the appended claims.

Having thus described my invention, what I desire to secure by Letters Patent is the following:

1. A method for protecting patients against chemically induced cytotoxic injury from tacrine, comprising the step of:

administering to a patient who will be provided with tacrine, prior to said patient receiving tacrine, an effective amount of an ionizable congener of a sterol compound having the formula:

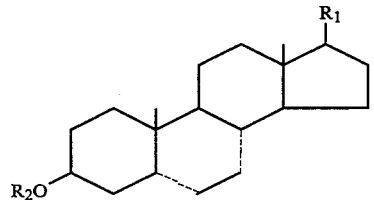

where the dashed lines denote either a single or double bond between the carbons, $R_1$ is an alkyl moiety, and $R_2$ is an ionizable moiety selected from the group consisting of succinate, sulfate, and phthalate and subsequently administering tacrine to said patient.

* * * * *